US008890097B2

(12) United States Patent
Iwata

(10) Patent No.: US 8,890,097 B2
(45) Date of Patent: Nov. 18, 2014

(54) MULTI-LEAF COLLIMATOR, PARTICLE BEAM THERAPY SYSTEM, AND TREATMENT PLANNING APPARATUS

(71) Applicant: Mitsubishi Electric Corporation, Chiyoda-ku (JP)

(72) Inventor: Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/263,594

(22) Filed: Apr. 28, 2014

(65) Prior Publication Data

US 2014/0235919 A1 Aug. 21, 2014

Related U.S. Application Data

(63) Continuation of application No. 13/696,931, filed as application No. PCT/JP2010/063874 on Aug. 17, 2010, now Pat. No. 8,754,386.

(51) Int. Cl.
*A61N 5/10* (2006.01)

(52) U.S. Cl.
CPC .............. *A61N 5/1045* (2013.01); *A61N 5/103* (2013.01)
USPC ...................... 250/492.3; 250/505.1; 378/153

(58) Field of Classification Search
CPC ......... A61N 5/00; A61N 5/10; A61N 5/1042; A61N 5/1045; A61N 5/1047; H01J 37/08; H01J 37/09; H01J 37/30; H01J 37/3447
USPC .......... 250/492.1, 492.3, 505.1; 378/147–153
See application file for complete search history.

(56) References Cited

U.S. PATENT DOCUMENTS 4,882,741 A 11/1989 Brown
5,144,647 A * 9/1992 Kikuchi ........................ 378/153
(Continued)

FOREIGN PATENT DOCUMENTS

JP 60-063500 A 4/1985
JP 63-225199 A 9/1988
(Continued)

OTHER PUBLICATIONS

International Search Report (PCT/ISA/210) issued on Sep. 14, 2010, by the Japanese Patent Office as the International Searching Authority for International Application No. PCT/JP2010/063874.
Office Action issued Nov. 27, 2013 in a corresponding Taiwanese patent application and English-language translation, 7 pages.

*Primary Examiner* — Michael Logie
*Assistant Examiner* — David E Smith
(74) *Attorney, Agent, or Firm* — Buchanan Ingersoll & Rooney PC

(57) ABSTRACT

There are provided a leaf row in which a plurality of leaf plates are arranged in the thickness direction of the row in such a way that the respective one end faces of the leaf plates are trued up and a leaf plate drive mechanism that drives each of the plurality of leaf plates in such a way that the one end face approaches or departs from a beam axis. In each of the leaf plates, a facing side facing a leaf plate that is adjacent to that leaf plate in the thickness direction is formed of a plane including a first axis on the beam axis; the leaf plate drive mechanism drives the leaf plate along a circumferential orbit around the second axis, on the beam axis, that is perpendicular to the beam axis and the first axis.

21 Claims, 8 Drawing Sheets

(56) References Cited

U.S. PATENT DOCUMENTS

| | | | | |
|---|---|---|---|---|
| 7,919,759 | B2 | 4/2011 | Furukawa et al. | |
| 2004/0062354 | A1 | 4/2004 | Kato et al. | |
| 2005/0063516 | A1* | 3/2005 | Kato et al. | 378/152 |
| 2008/0006776 | A1 | 1/2008 | Furukawa et al. | |
| 2008/0205599 | A1* | 8/2008 | Hashimoto | 378/148 |
| 2009/0003524 | A1 | 1/2009 | Pu | |
| 2009/0262901 | A1* | 10/2009 | Broad et al. | 378/152 |
| 2010/0166150 | A1* | 7/2010 | Perkins et al. | 378/148 |
| 2010/0228116 | A1* | 9/2010 | Lu et al. | 600/411 |

FOREIGN PATENT DOCUMENTS

| | | | |
|---|---|---|---|
| JP | 4-067875 | A | 3/1992 |
| JP | 10-255707 | A | 9/1998 |
| JP | 2004-121654 | A | 4/2004 |
| JP | 2006-166947 | A | 6/2006 |
| JP | 2008-229324 | A | 10/2008 |
| JP | 2009-268940 | A | 11/2009 |
| JP | 2010-012056 | A | 1/2010 |

* cited by examiner

MULTI-LEAF COLLIMATOR, PARTICLE BEAM THERAPY SYSTEM, AND TREATMENT PLANNING APPARATUS

RELATED APPLICATIONS

This application is a continuation of U.S. application Ser. No. 13/696,931, filed on Nov. 8, 2012, which claims priority from International Application No. PCT/JP2010/063874, filed on Aug. 17, 2010, the contents of which are herein incorporated in their entirety by reference.

TECHNICAL FIELD

The present invention relates to a multi-leaf collimator that is utilized in order to form an irradiation field in a particle beam therapy system utilizing a charged particle beam, relates to a particle beam therapy system utilizing the multi-leaf collimator, and relates to a treatment planning apparatus for determining the operation condition of the particle beam therapy system.

BACKGROUND ART

In the particle beam therapy, therapy is implemented by irradiating a charged particle beam onto a diseased site, which is a therapy subject, so as to kill tissues of the diseased site; in order to deliver a sufficient dose to the tissues of the diseased site without causing damage to the peripheral tissues thereof, there is required a particle beam therapy system that can appropriately control an irradiation dose and irradiation coverage (referred to as an irradiation field, hereinafter). In a so-called broad-irradiation-type particle beam therapy system, among particle beam therapy systems, that utilizes an irradiation nozzle provided with a scanning electromagnet such as a wobbler electromagnet, the irradiation nozzle enlarges the irradiation field and a multi-leaf collimator that changes a penetration shape is disposed in the enlarged irradiation field, so that an irradiation field corresponding to the shape of a diseased site is formed.

A multi-leaf collimator, in which two leaf lines formed of leaf plates laminated in the thickness direction are arranged in such a way as to face each other and the leaf plates are driven in a direction in which they approach each other or in a direction in which they are separated from each other, forms a predetermined penetration shape. Accordingly, by controlling the respective physical positions of the leaf plates, an irradiation field can readily be formed. However, in the case of a linear-driven leaf plate, in the contour portion that is away from the center of the irradiation field, a so-called penumbra is caused in which a charged particle beam having an angle toward the spreading direction hits part of the end face of the leaf plate and hence the dose of the charged particle beam is continuously attenuated. Thus, a so-called cone-shaped multi-leaf collimator has been proposed (e.g., refer to Patent Document 1 or 2) in which the spread of a beam is taken into consideration and leaves formed in a shape obtained through division at the side surface of an arc or a cone are driven on a circular orbit.

PRIOR ART REFERENCE

Patent Document

[Patent Document 1] Japanese Patent Application Laid-Open No. S60-063500 (top right of Page 2, down right of Page 2 to top left of Page 3, and FIGS. 2 and 4)

[Patent Document 2] Japanese Patent Application Laid-Open No. S63-225199 (down right of Page 3 to top right of Page 4, down left to down right of Page 7, FIGS. 1 through 3, and FIGS. 12 and 13)

[Patent Document 3] Japanese Patent Application Laid-Open No. 10-255707 (Paragraphs 0009 through 0020, and FIGS. 1 and 5)

[Patent Document 4] Japanese Patent Application Laid-Open No. 2006-166947 (paragraphs 0015 to 0016, and FIG. 1)

DISCLOSURE OF THE INVENTION

Problems to be Solved by the Invention

However, in the case of the foregoing cone-shaped multi-leaf collimator, it is assumed that a beam spreads from a point light source. Alternatively, even in the case where it is assumed that the light source is a volume light source, it is not taken into consideration that the spreading manner differs depending on the direction. On the other hand, in order to enlarge an irradiation field in a particle beam therapy system that utilizes a charged particle beam, there is required an electromagnet for scanning a thin beam supplied from the accelerator, as described in Patent Documents 3 and 4. On top of that, there are required respective electromagnets such as an X-direction electromagnet and a Y-direction electromagnet for two directions in a plane perpendicular to the beam axis; thus, the spread starting point in the X direction and the spread starting point in the Y direction differ from each other. Accordingly, there has been a problem that even when the foregoing multi-leaf collimator is applied to a particle beam therapy system, the beam spreading manner and the penetration shape of the multi-leaf collimator do not coincide with each other and hence a penumbra remains.

The present invention has been implemented in order to solve the foregoing problems; the objective thereof is to obtain a multi-leaf collimator and a particle beam therapy system in which a high-contrast irradiation field can be formed without undergoing the effect of a penumbra.

Means for Solving the Problems

A multi-leaf collimator according to the present invention is disposed in a particle beam that is irradiated so as to enlarge an irradiation field of that, in order to form the irradiation field so as to be conformed to an irradiation subject; the multi-leaf collimator is characterized in that there are provided a leaf row in which a plurality of leaf plates are arranged in the thickness direction thereof in such a way that the respective one end faces of the leaf plates are trued up and a leaf plate drive mechanism that drives each of the plurality of leaf plates in such a way that the one end face approaches or departs from a beam axis of the particle beam, in that in each of the leaf plates, a facing side facing a leaf plate that is adjacent to that leaf plate in the thickness direction is formed of a plane including a first axis that is perpendicular to the beam axis and is set at a first position on the beam axis, and in that the leaf plate drive mechanism drives the leaf plate along a circumferential orbit around a second axis that is perpendicular to the beam axis and the first axis and is set at a second position on the beam axis.

A particle beam therapy system according to the present invention is characterized by including an irradiation nozzle that scans a particle beam supplied from an accelerator, by use of two electromagnets whose scanning directions are different from each other, and that irradiates the particle beam in such a way as to enlarge an irradiation field and the multi-leaf collimator, disposed in a particle beam irradiated from the irradiation nozzle, and characterized in that the multi-leaf collimator is disposed in such a way that the first axis coincides with the scanning axis of one of the two electromagnets and the second axis coincides with the scanning axis of the other one of the two electromagnets.

A particle beam therapy system according to the present invention is characterized by including a three-dimensional data generation unit for generating three-dimensional data from image data on an irradiation subject, an irradiation condition setting unit that sets an irradiation condition, based on the generated three-dimensional data, and a control data generation unit that generates control data for controlling leaf driving for the multi-leaf collimator in the foregoing particle beam therapy system, based on the set irradiation condition, and characterized in that the three-dimensional data generation unit generates the three-dimensional data by utilizing at least a beam deflection angle with respect to the first axis and a beam deflection angle with respect to the second axis.

Advantage of the Invention

In a multi-leaf collimator, a particle beam therapy system, and a treatment planning apparatus according to the present invention, the directions of the faces of leaf plates that configure a contour at a time when the multi-leaf collimator forms a penetration shape coincide with the directions of a particle beam spreading and passing through the vicinity of the faces; thus, a high-contrast irradiation field can be formed without undergoing the effect of a penumbra.

BEST MODE FOR CARRYING OUT THE INVENTION

Embodiment 1

Figure 1:
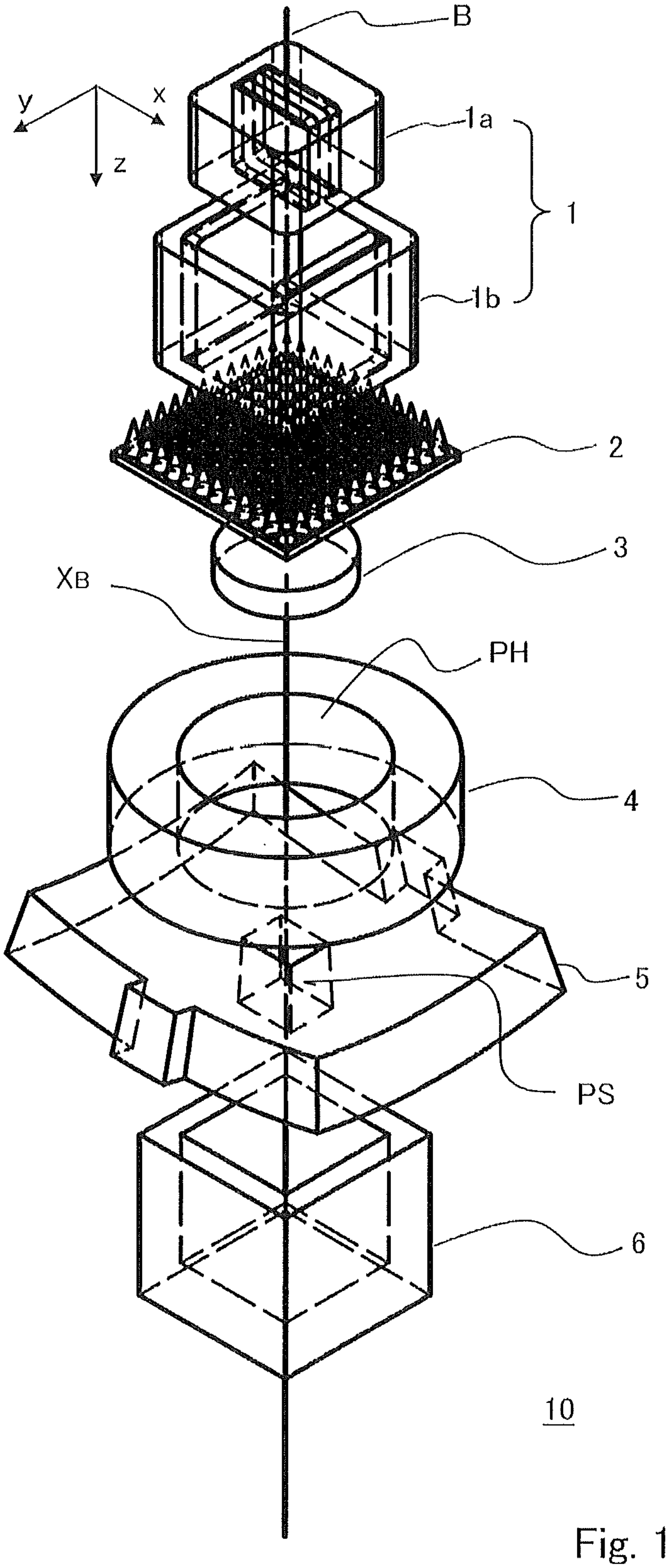
FIG. 1 is a view for explaining the configuration of an irradiation system, of a particle beam therapy system, that is provided with a multi-leaf collimator according to Embodiment 1 of the present invention.
Figure 2:
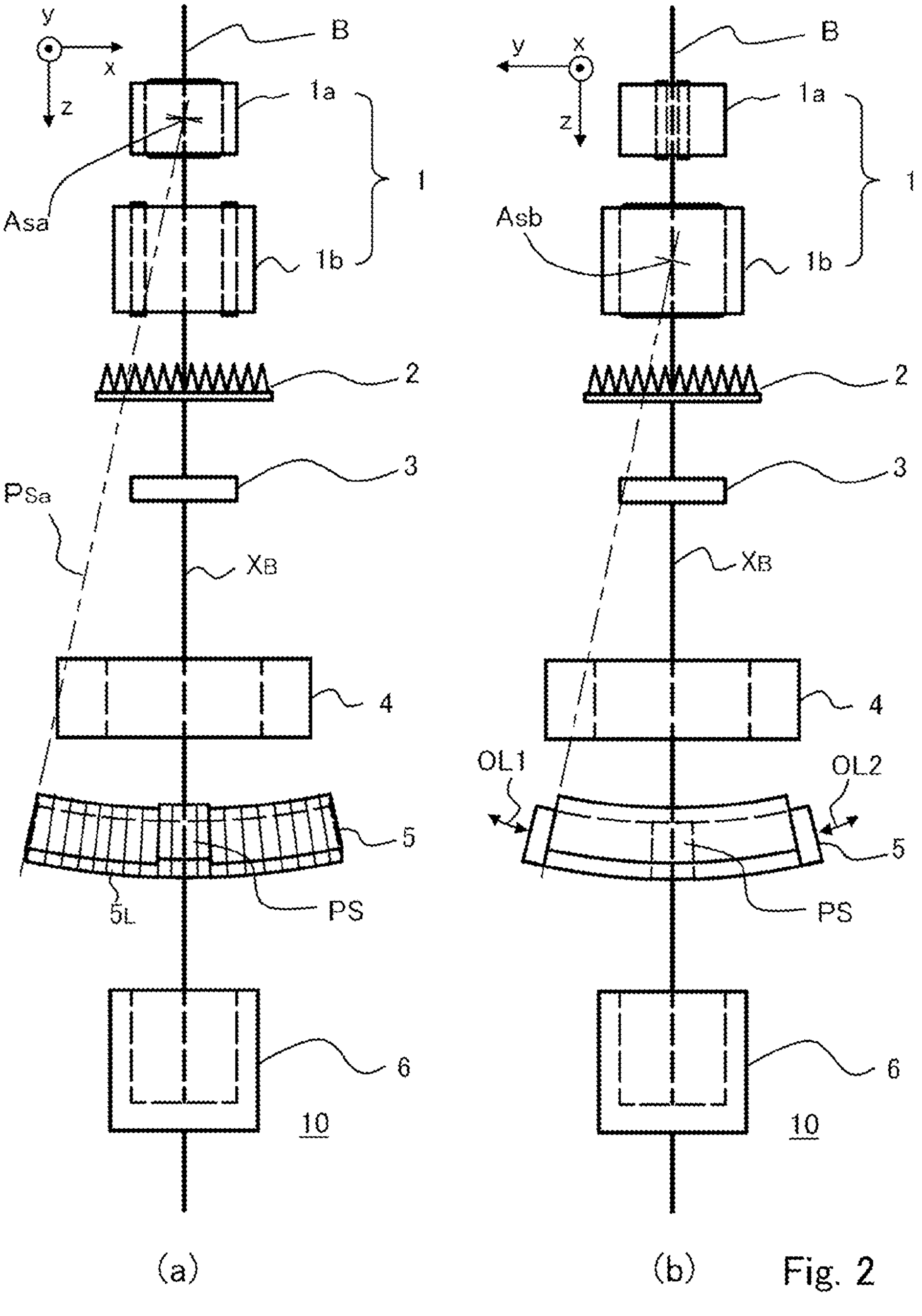
FIGS. 2(*a*) and (*b*) depict views for explaining the configuration of an irradiation system, of a particle beam therapy system, that is provided with a multi-leaf collimator according to Embodiment 1 of the present invention, when the irradiation system is viewed from two directions that are perpendicular to each other with respect to the center of a beam.
Figure 3:
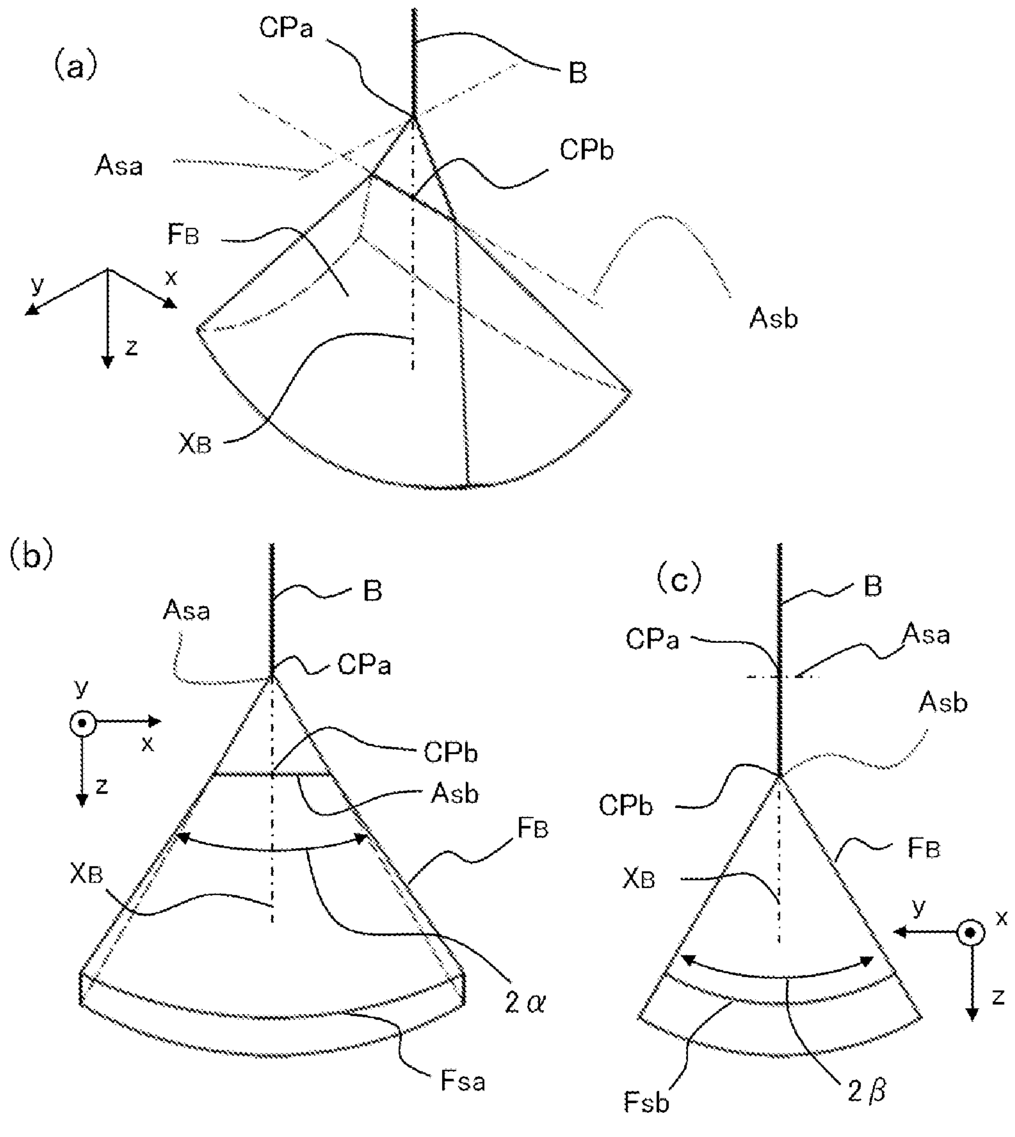
FIGS. 3(*a*)-(*c*) depict views for explaining the beam-bundle state of a charged particle beam in an irradiation system of a particle beam therapy system according to Embodiment 1 of the present invention.
Figure 4:
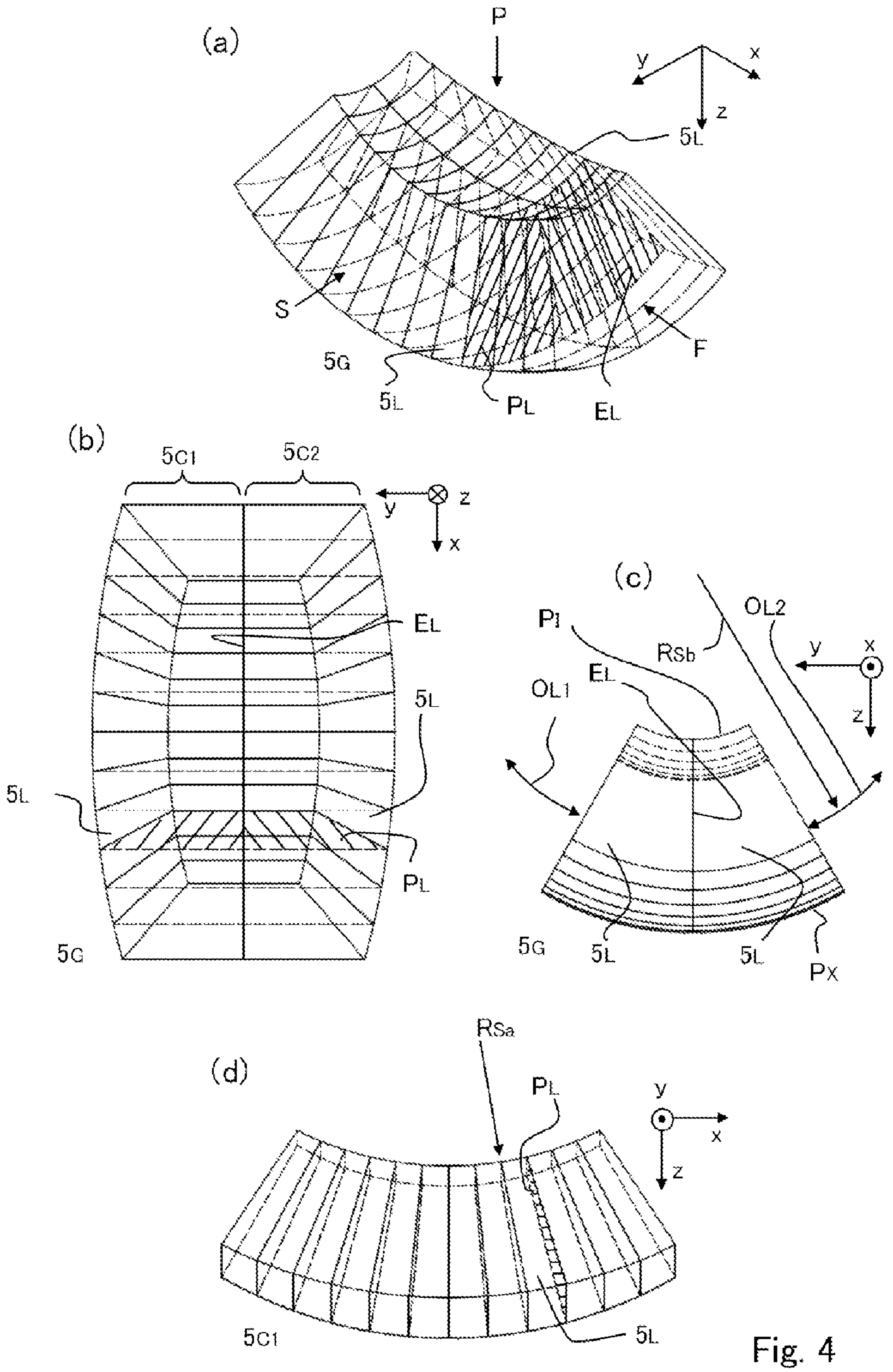
FIGS. 4(*a*)-(*d*) depict views for explaining the configurations of a multi-leaf collimator and a leaf plate according to Embodiment 1 of the present invention, when the leaves are all closed.
Figure 5:
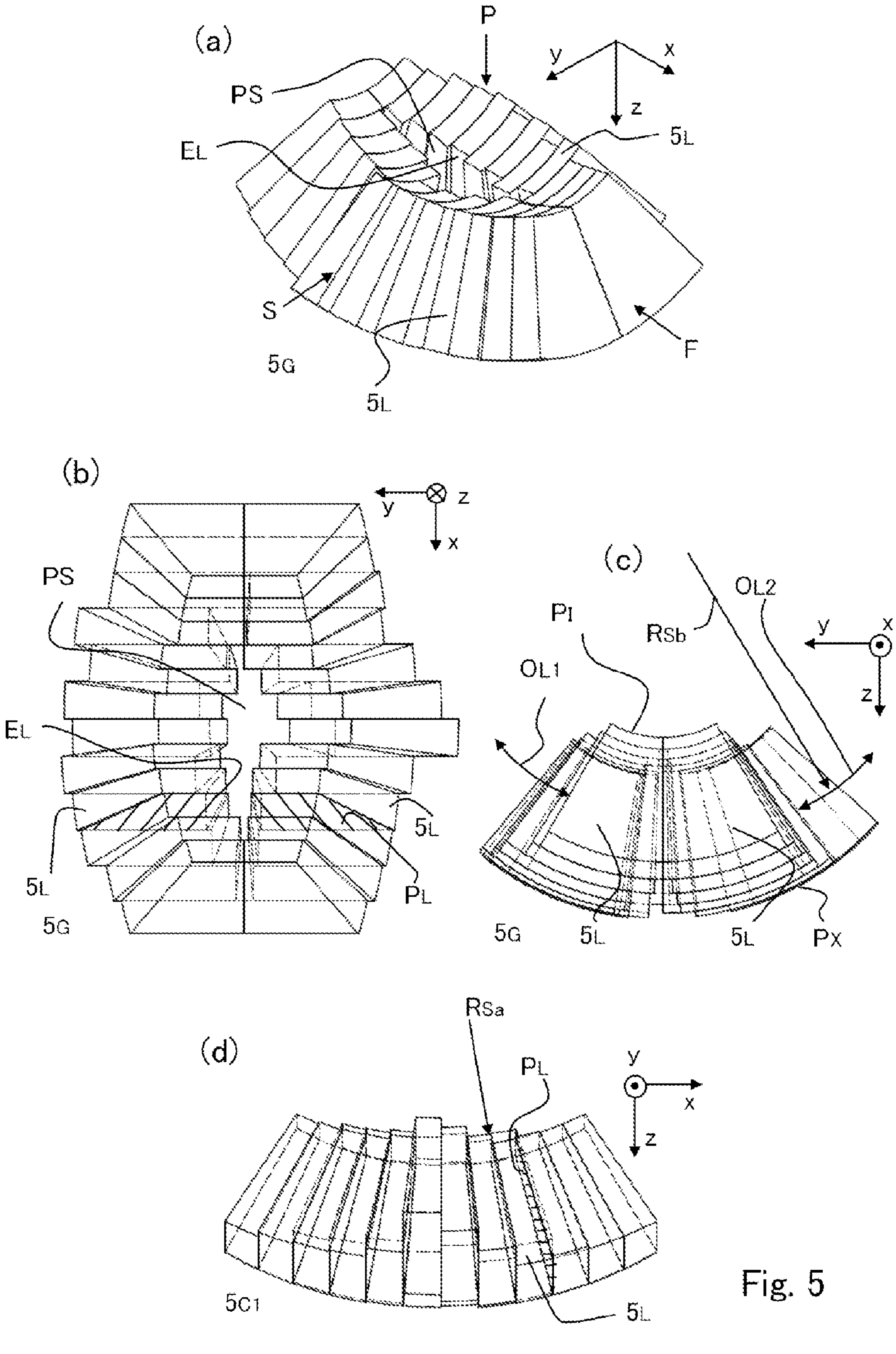
FIGS. 5(*a*)-(*d*) depict views for explaining the configurations of a multi-leaf collimator and a leaf plate according to Embodiment 1 of the present invention, when an irradiation field having a predetermined shape is formed.

The configurations of a multi-leaf collimator and a particle beam therapy system according to Embodiment 1 of the present invention will be explained below. FIGS. 1 through 5 are to explain the configurations of a multi-leaf collimator and a particle beam therapy system according to Embodiment 1 of the present invention. FIG. 1 is a view illustrating the configuration of an irradiation system, of a particle beam therapy system, that is provided with a multi-leaf collimator. FIG. 2 is a set of views for illustrating the configurations of a particle beam therapy system and a multi-leaf collimator when they are viewed from directions that are perpendicular to each other with respect to the center (z direction) of a charged particle beam in FIG. 1; FIG. 2(*a*) is a side view when viewed from the y direction; FIG. 2(*b*) is a side view when viewed from the x direction. FIG. 3 is to explain the shape of a beam bundle in an irradiation system of a particle beam therapy system; FIG. 3(*a*) is a view illustrating the overall appearance of a beam bundle; FIGS. 3(*b*) and 3(*c*) are views of the beam bundle when viewed from directions that are perpendicular to each other with respect to the center (z direction) of a charged particle beam in FIG. 3(*a*); FIG. 3(*b*) is a side view when viewed from the y direction; FIG. 3(*c*) is a side view when viewed from the x direction. Each of FIGS. 4 and 5 is a set of views for explaining the configurations of a multi-leaf collimator and a leaf plate, which is a main constituent member of the multi-leaf collimator, when viewed from various directions.

At first, as an assumption for a detailed explanation about the configuration of a multi-leaf collimator, an irradiation system, of a particle beam therapy system, that includes a multi-leaf collimator will be explained. As illustrated in FIGS. 1 and 2, a particle beam therapy system 10 is provided with a wobbler electromagnet 1 (an upstream wobbler electromagnet 1*a*, a downstream wobbler electromagnet 1*b*) that functions as an irradiation nozzle for enlarging an irradiation field by circularly scanning the charged particle beam B, which is supplied from an unillustrated accelerator and has a so-called pencil-looking shape; a ridge filter 2 for enlarging the width of a Bragg peak in accordance with the thickness of an irradiation subject; a range shifter 3 for changing the energy (range) of the charged particle beam B in accordance with the depth (irradiation depth) of the irradiation subject; a block collimator 4 for limiting the enlarged irradiation field to a predetermined area so as to prevent superfluous irradiation onto normal tissues; a multi-leaf collimator 5 that is configured with a plurality of leaf plates and a leaf drive mechanism for driving each of the leaf plates and that limits an irradiation field in such a way that the irradiation field coincides with the shape of a diseased site; and a bolus 6 that limits the range of the charged particle beam B in such a way that the range coincides with the depth-direction shape of an irradiation subject.

Next, there will be explained the operation and the principle of an irradiation system that enlarges an irradiation field by means of an irradiation nozzle in which the Wobbling method is utilized. The charged particle beam B is accelerated by the unillustrated accelerator; then, as a so-called pencil beam having a diameter smaller than several millimeters, it is introduced to the irradiation system through a transport system. The beam introduced to the irradiation system is scanned by the wobbler electromagnet 1 in such a way as to draw a circular orbit. As illustrated in FIG. 1 or 2, the wobbler electromagnet 1 is usually provided with an x-direction electromagnet 1*a* and a y-direction electromagnet 1*b*; the two electromagnets are arranged in such a way as to be superimposed on each other along the center axis $X_B$ of the charged particle beam B. Here, for clarity of description, the x direction and the y direction will be defined. In various specifications, coordinate systems are defined; however, in this "DESCRIPTION", the coordinate system is defined in the following manner. The direction in which the charged particle beam B travels is defined as the positive direction of the z axis. The x axis and the y axis are axes that are perpendicular to the z axis; the x axis and the y axis are also perpendicular to each other. Then, the xyz coordinate system is established in such a way as to be a right-handed coordinate system. In each of the examples in FIGS. 1 and 2, the upstream wobbler electromagnet 1*a* and the downstream wobbler electromagnet 1*b* scan a beam in the x direction and in the y direction, respectively. Due to the scanning by the electromagnets 1*a* and 1*b*, the irradiation field is expanded in the xy direction (planar direction).

The charged particle beam B whose irradiation field has been enlarged passes through the ridge filter 2. A ridge filter is formed, for example, in such a way that a great number of cones or plates whose cross sections are triangles are arranged on a plane; assuming that, for example, an irradiation field is divided into a great number of sub-areas, in which there exist beams that pass through different thicknesses from one another. For easier understanding, FIG. 1 or 2 illustrates cones that are arranged as in a pin holder ("kenzan"). In such a manner as described above, the width of a Bragg peak SOBP (Spread-Out Bragg Peak) is enlarged. That is to say, the ridge filter 2 enlarges the irradiation field also in the z direction. Next, the charged particle beam B whose irradiation field has been enlarged passes through the range shifter 3. The range shifter 3 is a device that changes the energy of the charged particle beam B. Due to the range shifter 3, the enlarged irradiation field can be irradiated onto a position of a desired inner-body depth. Next, the beam that has passed through the range shifter 3 passes through the block collimator 4. The block collimator 4 is, for example, a metal block in which a passing hole PH is provided, and limits the planar-direction (the xy plane) spread of the irradiation field. This is because superfluous irradiation onto normal tissues can be prevented by preliminarily limiting the irradiation coverage.

Next, the charged particle beam passes through the multi-leaf collimator 5. As described later, through a penetration shape PS formed based on the positions of a plurality of leaves $\mathbf{5}_L$, the multi-leaf collimator 5 limits the shape of the irradiation field in accordance with the shape of the diseased site. That is to say, the multi-leaf collimator 5 performs limitation and formation of the irradiation field in the xy direction. The multi-leaf collimator 5 is provided with at least the plurality of leaf plates $\mathbf{5}_L$ (collectively referred as a leaf group $\mathbf{5}_G$) and a leaf drive mechanism $\mathbf{5}_D$. However, the configuration of the leaf drive mechanism $\mathbf{5}_D$ itself is not important, as long as the driving orbit of a leaf can be specified. If the leaf drive mechanism $\mathbf{5}_D$ itself is drawn in a figure, it becomes difficult to illustrate the arrangement of the leaf plates $\mathbf{5}_L$; therefore, in FIGS. 1, 2, and thereafter, for the sake of simplicity, only a leaf plate $\mathbf{5}_L$ or only the leaf group $\mathbf{5}_G$ in which the leaf plates $\mathbf{5}_L$ are integrated, out of the multi-leaf collimator 5, is illustrated.

Lastly, the charged particle beam B passes through the bolus 6. The bolus 6 is a limiter that is formed of resin or the like; it is formed in such a shape as to compensate the depth-direction shape of a diseased site, for example, the distal shape of the diseased site. The distal shape denotes the depression-protrusion contour of the deepest portion. In this situation, the energy of the irradiation field is limited (formed in the z direction) to have a shape the same as the distal shape. That is to say, the bolus 6 performs limitation and formation of the irradiation field in the z direction.

The function of the irradiation system of a particle beam therapy system is to form an irradiation field in accordance with the diseased site onto which a beam is irradiated. In the Wobbling method that is adopted, as the method therefor, in a particle beam therapy system according to Embodiment 1, an irradiation field is enlarged only by the wobbler electromagnet 1. For example, the "large-area uniform irradiation method through spiral beam scanning" disclosed in Patent Document 3 is a specific example of this method, which is referred to as the "spiral Wobbling method", among the Wobbling methods. Briefly speaking, the spiral Wobbling method is to scan a beam in a spiral manner so as to enlarge an irradiation field; the scanning orbit (scanning locus) in the irradiation field is contrived so that the flatness is secured. Additionally, a beam scanning orbit according to the spiral Wobbling method can be seen in FIG. 1 and the like of Patent Document 1.

Meanwhile, in general, the method which is referred to as the "Wobbling method" often signifies the "single-circle Wobbling method"; in that case, when an irradiation field is enlarged, the flatness is secured by means of a scatterer. Therefore, among the Wobbling methods, there exist not only a Wobbling method in which a scatterer is utilized but also a Wobbling method in which no scatterer is utilized; thus, the directional behavior of a beam differs depending on whether or not there exists a scatterer. In the case where a scatterer is utilized, the beam spreads on the whole surface of the scatterer; thus, there exists a width in the irradiation direction of a beam that passes through a given point. In contrast, in the case where as the spiral Wobbling method, a beam is enlarged only by means of a scanning electromagnet without utilizing any scatterer, the irradiation direction of the beam that passes through a given point is a single direction that is determined mainly by the position thereof with respect to the scanning electromagnet.

FIG. 3 is a set of schematic diagrams illustrating the spreading manner (the shape of a beam bundle $F_B$) in which a beam is enlarged by the couple of scanning electromagnets 1 in the irradiation system of the particle beam therapy system 10 according to Embodiment 1. In the spiral Wobbling method, the beam is enlarged not in a point-light-source manner but in such a manner as illustrated in FIG. 3. For the sake of simplicity, the spreading manner of the beam, illustrated in FIG. 3, will be referred to as a "series-of-scanners spreading manner". In the case where a beam is enlarged not in a point-light-source manner but in a series-of-scanners spreading manner, a limiter suitable therefor needs to be designed.

The series-of-scanners spread will be explained in more detail hereinafter. As illustrated in FIG. 3, the beam B is irradiated from the top to the bottom (in the z direction). Originally, the beam B is supplied as a thin beam, which is called a pencil beam. Reference points CPa and CPb are set on the beam axis $X_B$. The reference point CPa may be regarded as a position where the upstream wobbler electromagnet 1*a* (strictly speaking, a scanning axis $A_{Sa}$) is disposed; similarly, the reference point CPb may be regarded as a position where the downstream wobbler electromagnet 1*b* (strictly speaking, a scanning axis $A_{Sb}$) is disposed.

The upstream wobbler electromagnet 1*a* disposed at the reference point CPa scans the beam B with respect to the reference point CPa. The scanning direction, of the upstream wobbler electromagnet 1*a*, in which the beam B is scanned is on a plane (the xz plane) of FIG. 3(*b*) and passes through the reference point CPa on the beam axis $X_B$; the axis $A_{Sa}$, which is perpendicular to the beam axis $X_B$, is the action axis (scanning axis) of the upstream wobbler electromagnet 1*a*. The downstream wobbler electromagnet 1*b* disposed at the reference point CPb scans the beam B with respect to the reference point CPb. The scanning direction, of the downstream wobbler electromagnet 1*b*, in which the beam B is scanned is on a plane (the yz plane) of FIG. 3(*c*) and passes through the reference point CPb on the beam axis $X_B$; the axis $A_{Sb}$, which is perpendicular to the beam axis $X_B$ and the axis $A_{sa}$, is the action axis (scanning axis) of the downstream wobbler electromagnet 1*b*. In other words, the scanning direction (x) of the upstream wobbler electromagnet 1*a* and the scanning direction (y) of the downstream wobbler electromagnet 1*b* are perpendicular to the beam axis $X_B$; the scanning direction (x) of the upstream wobbler electromagnet 1*a* and the scanning direction (y) of the downstream wobbler electromagnet 1*b* are perpendicular to each other.

Furthermore, the shape of the beam bundle $F_B$ will geometrically be explained with reference to FIG. 3. As illustrated in FIG. 3(*b*), there is drawn a vertical (z-direction) line whose top end point is the reference point CPa, and then the reference point CPb is provided at a position other than the reference point CPa on the vertical line. There is obtained a sector Fsa through which the line passes when the line is pivoted by ±α° with respect to the reference point CPa. In the case where only the upstream wobbler electromagnet 1*a* is utilized, the sector Fsa corresponds to the spread of the beam. Next, the sector Fsa is divided into the upper part and the lower part by the reference axis $A_{sb}$ that passes through the reference point CPb. There is obtained a region through which the lower part of the sector Fsa passes when the lower part of the sector Fsa is pivoted by ±β° with respect to the reference axis $A_{sb}$. This region is recognized as a sector Fsb in FIG. 3(*c*) and represents the spreading manner (the region through which the beam B can pass: the beam bundle $F_B$) of the beam B. That is to say, the shape of the beam bundle $F_B$ having a series-of-scanners spread is a sector whose x-direction and y-direction curvature radiuses are different from each other.

By considering the shape of the beam bundle $F_B$ having a series-of-scanners spread that is caused by enlarging an irradiation field by means of two scanning electromagnets 1*a* and 1*b* whose scanning directions are different from each other, as described above, the multi-leaf collimator 5 according to Embodiment 1 of the present invention is configured for the purpose of accurately forming a high-contrast irradiation field without undergoing the effect of a penumbra. In other words, in the multi-leaf collimator 5 according to Embodiment 1 of the present invention, each of the leaf plates $\mathbf{5}_L$ is configured in such a way that the substantial facing side $P_L$ facing the adjacent leaf plate in the thickness direction is formed of a plane including the scanning axis $A_{sa}$, of the scanning electromagnet 1*a*, that is set at the reference point CPa on the beam axis XB of the charged particle beam B, and each of the leaf plates $\mathbf{5}_L$ is driven along a circumferential orbit with respect to the scanning axis $A_{sb}$, of the scanning electromagnet 1*b*, that is set at the reference point CPb on the beam axis $X_B$ and is perpendicular to the beam axis $X_B$ and the scanning axis $A_{sa}$.

Detailed explanation will be made below with reference to FIGS. 4 and 5. FIG. 4 is a set of views for explaining the configurations of a multi-leaf collimator and leaf plates to be driven in the multi-leaf collimator, when the leaves are all closed; FIG. 4(*a*) is an appearance perspective view of all the leaf group of the multi-leaf collimator; FIG. 4(*b*) is a top perspective view of the multi-leaf collimator when viewed from P direction in FIG. 4(*a*); FIG. 4(*c*) is a front perspective view of the multi-leaf collimator when viewed from F direction in FIG. 4(*a*); FIG. 4(*d*) is a side perspective view of a row of leaves in the left-half portion of the multi-leaf collimator, when viewed from S direction in FIG. 4(*a*). FIG. 5 is a set of views illustrating the state where an irradiation field having a predetermined shape is formed; FIG. 5(*a*) is an appearance view of all the leaf group of a multi-leaf collimator; FIG. 5(*b*) is a top perspective view of the multi-leaf collimator when viewed from P direction in FIG. 5(*a*); FIG. 5(*c*) is a front perspective view of the multi-leaf collimator when viewed from F direction in FIG. 5(*a*); FIG. 5(*d*) is a side perspective view of a row of leaves in the left-half portion of the multi-leaf collimator, when viewed from S direction in FIG. 5(*a*).

As illustrated in FIGS. 4 and 5, the multi-leaf collimator 5 is provided with a leaf group $\mathbf{5}_G$ that has two leaf rows ($\mathbf{5}_{c1}$ and $\mathbf{5}_{c2}$: collectively referred to as $\mathbf{5}_c$), in each of which a plurality of leaf plates $\mathbf{5}_L$ are arranged in the thickness direction (x direction) in such a way that the end faces $E_L$ thereof are trued up, and in which the leaf rows $\mathbf{5}_{c1}$ and $\mathbf{5}_{c2}$ are arranged in such a way that the respective end faces $E_L$ thereof face each other and with an unillustrated leaf plate drive mechanism that drives each of the leaf plates $\mathbf{5}_L$ in a direction in which that leaf plate approaches the opposed leaf plate or in a direction in which that leaf plate departs from the opposed leaf plate; as the shape of the leaf plate $\mathbf{5}_L$, the substantial shape of the main face as the plate material of each leaf plate, i.e., the facing side $P_L$ facing the adjacent leaf plate is formed of a plane including the scanning axis $A_{sa}$ of the scanning electromagnet 1*a* that enlarges the charged particle beam B in the x direction. In other words, the main plane as the plate material is formed of two planes including the scanning axis $A_{sa}$ of the scanning electromagnet 1*a*; the cross-section of the leaf plate, obtained by cutting the leaf plate along the plane including the irradiation direction and the board-thickness direction, becomes thicker in a direction from the upstream side of the irradiation direction of the charged particle beam B to the downstream side thereof.

The drive (in the yz-plane direction) of the leaf plates $\mathbf{5}_L$ is set to be an circumferential orbit $O_L$ corresponding to a distance $R_{sb}$ from the scanning axis $A_{sb}$ of the downstream electromagnet 1*b* that enlarges the charged particle beam B in the y direction, and the shapes of an incident-side end face $P_I$ that is adjacent to the end face $E_L$ and an emitting-side end face $P_X$, among the four end faces of the leaf plate $\mathbf{5}_L$, are each formed of an arc whose center is the scanning axis $A_{sb}$, i.e., each formed as if it is part of a ring whose center is the scanning axis $A_{sb}$, so that even when the leaf plate $\mathbf{5}_L$ is driven along the circumferential orbit $O_L$, the thickness dimension along the irradiation direction of the charged particle beam B does not change.

Because of the foregoing configuration, in whichever position the leaf plate $\mathbf{5}_L$ is driven, for example, as illustrated in FIG. 5, the end face $E_L$ of the leaf plate $\mathbf{5}_L$ that forms the x-direction contour of the penetration shape PS is in parallel with the irradiation direction of the charged particle beam B that passes through the vicinity of the end face $E_L$, whereby no penumbra is caused. The facing side $P_L$ of the leaf plate $\mathbf{5}_L$ that forms the y-direction contour of the penetration shape PS is in parallel with the irradiation direction of the charged particle beam B that passes through the vicinity of the facing side $P_L$, whereby no penumbra is caused. In other words, no penumbra is caused in any contour portion of the penetration shape PS formed by the multi-leaf collimator 5; therefore, an accurate irradiation field suited to the shape of a diseased site can be formed.

That is to say, it is only necessary that the thickness-direction shape and the driving orbit $O_L$ of the leaf plate $\mathbf{5}_L$ in the multi-leaf collimator 5 according to Embodiment 1 of the present invention form a shape the same as the spread of the beam bundle $F_B$ of the charged particle beam B. That is to say, the spread is the passable range at a time when the respective scanning angles of the couple of scanning electromagnets 1*a* and 1*b* are limited. Furthermore, the spread is the position of a charged particle beam at a time when the beam propagation distance from the beam source is within a given range. Because the multi-leaf collimator 5 is obtained by laminating the leaf plates $\mathbf{5}_L$, the formed penetration shape PS is also the spread shape of the beam bundle $F_B$ of a charged particle beam. Moreover, because of the foregoing configuration, whatever the shape of the opening (contour) that forms the penetration shape PS is, the end face $E_L$, of the leaf plate $\mathbf{5}_L$, that is a wall face of the opening and faces the center of the irradiation field and the facing side $P_L$ facing the adjacent leaf plate are in parallel with the irradiation direction of a charged particle beam that passes through the vicinity of those faces. Accordingly, the problem of a penumbra, caused when a couple of scanning electromagnet 1*a* and 1*b* are utilized, can be solved. In the case where irradiation is implemented by use of a scatterer for the purpose of raising the flatness, a range in the distribution of the irradiation directions is caused by the foregoing series-of-scanners manner. Accordingly, because even in the case where the multi-leaf collimator 5 is utilized, some of charged particle beams hit the end face $E_L$ of the leaf plate or the facing side $P_L$, the effect of suppressing a penumbra is reduced in comparison with the case where no scatterer is utilized; however, it is made possible to obtain a larger effect of suppressing a penumbra in comparison with a simple cone-shaped conventional multi-leaf collimator.

In the multi-leaf collimator 5 according to Embodiment 1, the thickness-direction shape and the driving orbit $O_L$ are set based on the position of the upstream electromagnet 1*a* and the position of the downstream electromagnet 1*b*, respectively; however, the present invention is not limited thereto. They may be set on the opposite positions. Accordingly, there has been described that the upstream electromagnet 1*a* and the downstream electromagnet 1*b* scan a beam in the x direction and in the y direction, respectively; however, they may scan a beam in an opposite manner. Although the drawings illustrate that the angles, between the facing sides PL are uniform, that specify the thickness of the leaf plate 5L; however, the present invention is not limited thereto. Even when the angles are not uniform, it is made possible to obtain the effect of suppressing a penumbra. The reason why the expression "substantial" is utilized for the facing side is to mean that the facing side is a side for distinguishing it from the leaf that is substantially adjacent to it when the leaves are laminated in the thickness direction; for example, even when a groove or a recess for forming a driving rail is provided in the facing side, it is understood that the facing side is formed of a plane including the scanning axis $A_{sa}$ of the scanning electromagnet 1*a* set at the reference point CPa. The drawings illustrate the state where one of the leaves $\mathbf{5}_L$ of the leaf row $\mathbf{5}_{c1}$ and one of the leaves $\mathbf{5}_L$ of the leaf row $\mathbf{5}_{c2}$ make a pair; however, they do not necessarily need to make a pair. The number of the leaf rows does not need to be two; for example, even when the number of the leaf rows is one, it is only necessary that when the end face $E_L$ of the leaf plate becomes closest to the beam axis $X_B$, the end face $E_L$ adheres to the fixed side so as to block the beam B. The number of the leaf rows may be more than two.

As a method of enlarging an irradiation field, there has been explained a spiral Wobbling method in which a scanning locus becomes a spiral; however, as explained in the following embodiments, another spiral Wobbling method may be utilized, and the method may not be limited to a spiral Wobbling method. Moreover, the electromagnet that functions as an irradiation nozzle is not limited to the wobbler electromagnet 1; it is only necessary that the irradiation nozzle is to enlarge an irradiation field by means of two electromagnets whose scanning directions are different from each other.

As described above, the multi-leaf collimator 5 according to Embodiment 1 is disposed in the charged particle beam B that is irradiated by use of the scanning electromagnet 1 so as to enlarge an irradiation field of that, in order to form the irradiation field so as to be conformed to the shape of a diseased site, which is an irradiation subject; the multi-leaf collimator 5 is provided with the leaf row $\mathbf{5}_c$ in which a plurality of leaf plates $\mathbf{5}_L$ are arranged in the thickness direction in such a way that the end faces $E_L$ thereof are trued up and with the leaf plate drive mechanism $\mathbf{5}_D$ that drives each of the leaf plates $\mathbf{5}_L$ in such a way that the end face $E_L$ thereof approaches or departs from the beam axis $X_B$ of the particle beam B or that drives each of the leaf plates $\mathbf{5}_L$ in a direction in which that leaf plate $\mathbf{5}_L$ approaches the opposed leaf plate or in a direction in which that leaf plate $\mathbf{5}_L$ departs from the opposed leaf plate. In each of the leaf plates $\mathbf{5}_L$, the facing side $P_L$ facing a leaf plate that is adjacent to that leaf plate in the thickness direction (x direction) is formed of a plane $P_{sa}$ including the scanning axis $A_{sa}$, which is a first axis perpendicular to the beam axis $X_B$ and is set at the reference point CPa that is a first position on the beam axis $X_B$ of the charged particle beam B; the leaf plate drive mechanism $\mathbf{5}_D$ drives the leaf plate $\mathbf{5}_L$ along the circumferential orbit $O_L$ around the scanning axis $A_{sb}$, which is a second axis perpendicular to the beam axis $X_B$ and the first axis $A_{sa}$, set at the reference point CPb that is a second position on the beam axis $X_B$. As a result, the spreading manner of the beam bundle $F_B$ of the charged particle beam B and the directions of the facing side $P_L$ and the end face $E_L$ that form the contour of the penetration shape PS of the multi-leaf collimator 5 coincide with each other, so that the effect of a penumbra is suppressed and hence an accurate irradiation field conforming to the shape of an irradiation subject can be formed.

Furthermore, the shapes of the end face $P_I$ at the incident side of the charged particle beam B and the end face $P_X$ at the emitting side thereof that are adjacent to the end face $E_L$, among the main four end faces of the leaf plate $\mathbf{5}_L$, are formed in the shape of an arc whose center is the scanning axis $A_{sb}$, which is the second axis; therefore, the leaf plate $\mathbf{5}_L$ can readily be driven along the circumferential orbit $O_L$. And whichever position the leaf plate 5L is driven, the depth dimension along the irradiation direction of the charged particle beam B does not change; therefore, the distance for shutting off the charged particle beam becomes constant.

The particle beam therapy system 10 according to Embodiment 1 of the present invention is provided with the wobbler electromagnet 1, which is an irradiation nozzle that scans the charged particle beam B supplied from an accelerator, by use of two electromagnets 1*a* and 1*b* whose scanning directions are different from each other and irradiates the charged particle beam B in such a way as to enlarge an irradiation field, and the foregoing multi-leaf collimator 5 that is disposed in the charged particle beam B (the beam bundle FB thereof)

irradiated from the irradiation nozzle 1; the multi-leaf collimator 5 is disposed in such a way that the first axis thereof coincides with the scanning axis ($A_{sa}$ or $A_{sb}$) of one of the two electromagnets and the second axis thereof coincides with the scanning axis ($A_{sb}$ or $A_{sa}$) of the other electromagnet. Therefore, the effect of a penumbra is suppressed and hence a charged particle beam can be irradiated with an accurate irradiation field conforming to the shape of an irradiation subject.

Embodiment 2

In Embodiment 1, there has been described the application of a multi-leaf collimator according to the present invention to the spiral Wobbling method in which a beam is scanned in a spiral manner. However, the technical idea of the present invention is not limited to the foregoing scanning orbit shape (scanning locus) in the irradiation field of a beam; the effect of the present invention is demonstrated even in the case of other beam scanning loci, as long as the spreading manner is a series-of-scanners manner. Thus, in Embodiment 2, there will be described a case where a multi-leaf collimator according to the present invention is applied to an irradiation system having another typical beam scanning locus.

At first, there will be explained a beam scanning locus produced through the spiral Wobbling method utilized in Embodiment 1. As disclosed in Patent Document 3, the spiral scanning locus is given by the equation (1) including the following three equalities.

$$r(t)=\sqrt{\frac{R_{max}-R_{min}}{\pi N}v_0 t+R_{min}^2} \quad (1)$$

$$\omega(t)=\frac{v_0}{\sqrt{\frac{R_{max}-R_{min}}{\pi N}v_0 t+R_{min}^2}}$$

$$\therefore \theta(t)=\theta(0)+\int_0^t \omega(\tau)\,d\tau$$

where $R_{min}$ is the radius at a time when the time t=0, $R_{max}$ is the radius at a time when the time t=T, and N is the scanning rotation speed. In addition, r(t) is the radial-direction coordinates, and θ(t) is the angle-direction coordinates; r(t) and θ(t) are represented through a polar coordinate system.

The shape of the beam scanning locus given by the equation (1) is spiral; the shape is effective in obtaining a uniform dose distribution by scanning a beam within a circular region. However, it is not required that in order to obtain a uniform dose distribution, the beam scanning locus is limited to a spiral locus. It is conceivable that the beam scanning loci for obtaining a uniform dose distribution through scanning by two electromagnets can be categorized into a number of typical patterns.

The Wobbling method is to form a uniform dose distribution by continuously scanning a beam. That is to say, it is desirable that the beam scanning locus in the Wobbling method is continuous and periodical. Thus, there has been studied a pattern in which a beam orbit is represented by a polar coordinate system and r(t) and θ(t) are continuously and periodically changed.

<Typical Pattern-1>

In the first pattern, r(t) and θ(t) are each defined as a function that changes continuously and periodically, as described below.

r(t)=continuous and periodic function (period: $T_1$)

θ(t)=continuous and periodic function (period: $T_2$)

In this situation, the respective periods of r(t) and θ(t), which are different from each other, may be utilized. Attention should be drawn to the fact that as for the angle θ, 360° can be regarded as 0° as it rotates once. In other words, 360° continues to 0°. When represented in radian, 2π can be regarded as 0.

Examples that realize the foregoing pattern include such a beam scanning locus as represented by the equation (2) including the following three equalities.

$$r(\tau)=r_1+r_2\sin(\omega_r\tau+\phi_r)$$

$$\theta(\tau)=\omega_\theta\tau$$

$$\tau=\tau(t) \quad (2)$$

where τ(t) is the parameter of the equation (2) that is represented by utilizing a parameter, and is the function of the time. $\omega_r$ is the angular velocity that determines r(t), and the period of r(t) is $2\pi/\omega_r$. $\phi_r$ is the initial phase. $\omega_\theta$ is the angular velocity that determines θ(t), and the period of θ(t) is $2\pi/\omega_\theta$.

Figure 6:
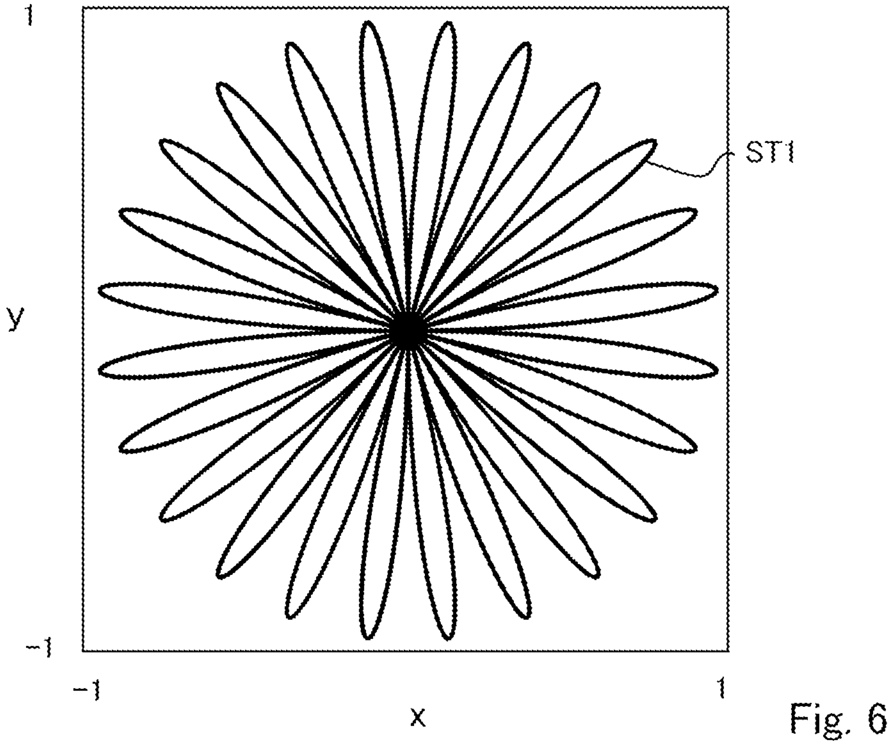
FIG. 6 is a chart representing an example of beam scanning locus in a particle beam therapy system according to Embodiment 2 of the present invention.

FIG. 6 represents an example of beam scanning locus ST1 generated according to the equation (2). FIG. 6 represents a scanning locus on a given plane that is perpendicular to the beam axis; the abscissa denotes "x" and the ordinate denotes "y"; x and y are each normalized. The reason why in the equation (2), the parameter is not the time is that it is required to make the drawing speed changeable depending on the place. For example, in FIG. 6, beam scanning concentrates in the vicinity of the center of the beam axis represented as the coordinates (0, 0); thus, in a portion in the vicinity of the center portion where the locus concentrates, contrivance such as raising the scanning speed is made so that a uniform dose distribution is obtained.

<Typical Pattern-2>

Figure 7:
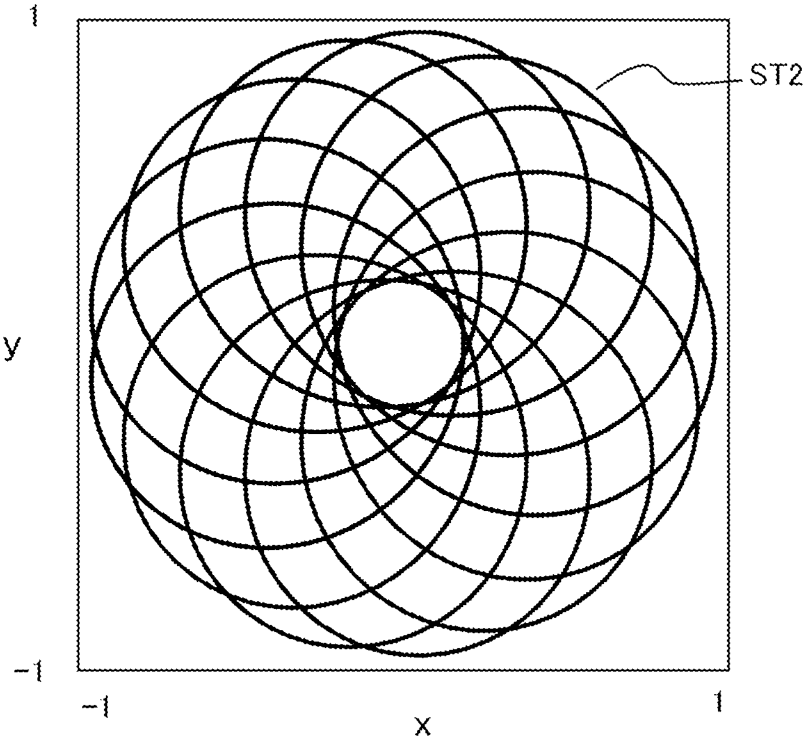
FIG. 7 is a chart representing another example of beam scanning locus in a particle beam therapy system according to Embodiment 2 of the present invention.

In the second pattern, two or more functions for defining a drawing pattern are combined so that a beam scanning locus is formed. For example, a function for drawing a large circle is combined with a function for drawing a small circle. An example is represented by the equation (3) including the following three equalities.

$$x(\tau)=r_1\cos(\omega_1\tau+\phi_1)+r_2\cos(\omega_2\tau+\phi_2)$$

$$y(\tau)=r_1\sin(\omega_1\tau+\phi_1)+r_2\sin(\omega_2\tau+\phi_2)$$

$$\tau=\tau(t) \quad (3)$$

where x(τ) and y(τ) are the x coordinate and the y coordinate, respectively, of a beam scanning locus; they are represented by use of an orthogonal coordinates system. FIG. 7 represents an example of beam scanning locus generated according to the equation (3). As is the case with FIG. 6, FIG. 7 represents a scanning locus on a given plane that is perpendicular to the beam axis; the abscissa denotes "x" and the ordinate denotes "y"; x and y are each normalized.

Among toys, there exists a tool in which a gear-shaped disk is disposed in a circular hole inside of which teeth are formed; a geometrical pattern is drawn by inserting a pen tip into a small hole provided at a predetermined position in the disk and rolling the disk along the circular hole. A geometrical pattern generated with the tool also belongs to this category. A curve drawn with this tool is referred to as a hypotrochoid; geometrically, the curve is defined as a locus drawn by a fixed point that is lr away from the center of a circle of a radius r when the circle of a radius r rolls without sliding along the inner circumference of a circle of a radius kr. In many mixing devices, the curve is adopted as the driving pattern for a mixing unit. The reason why the parameter is not the time t is that it is required to make the drawing speed changeable depending on the place, as is the case with the above example.

As described above, in the method in which through a wobbler electromagnet, a continuous and periodical pattern (line drawing) is drawn, the pattern is not necessarily a spiral. However, the idea in which by utilizing no scatterer but by contriving a beam orbit, large-area uniform irradiation is realized originates in the "spiral Wobbling method"; therefore, in some cases, each of these methods described in Embodiment 2 is also referred to as a broad-sense spiral Wobbling method. In addition, also in these broad-sense spiral Wobbling methods, a beam spreads not in a point-light-source manner but in a series-of-scanners manner.

In other words, also in the particle beam therapy system having an irradiation system utilizing the broad-sense spiral Wobbling method according to Embodiment 2, by utilizing the multi-leaf collimator described in Embodiment 1, the thickness-direction shape of the leaf plate and the driving orbit can be made the same as the spread of the beam bundle $F_B$ of the charged particle beam B. Accordingly, the formed penetration shape PS becomes the same as the shape of the beam bundle $F_B$ of the charged particle beam B; thus, whatever the shape of the opening that forms the penetration shape PS is, the end face that is a wall face of the opening and faces the center of the irradiation field and the facing side facing the adjacent leaf plate coincide with the irradiation direction of a charged particle beam. Accordingly, the problem of a penumbra, caused when a couple of scanning electromagnets are utilized, can be solved.

Embodiment 3

In each of Embodiments 1 and 2, there has been described a case where a multi-leaf collimator is applied to irradiation through the Wobbling method. However, as described above, the irradiation method itself is not essential and does not define the technical idea of the present invention. With regard to a particle beam therapy system, there has been proposed a spot-scanning method in which a charged particle beam is scanned by means of a couple of scanning electromagnets, and a spot is irradiated onto an irradiation subject in a pointillism manner. Also in the spot-scanning method, a beam spreads in a series-of-scanners manner. Therefore, in the case where a multi-leaf collimator is utilized in spot scanning, there is demonstrated an effect that a penumbra is suppressed and a high-contrast irradiation field is formed.

Embodiment 4

In Embodiment 3, there has been described the application of a multi-leaf collimator according to the present invention to the spot-scanning method. There exists a raster-scanning method in which a charged particle beam is scanned by means of a couple of scanning electromagnets, as is the case with a spot-scanning method, and raster irradiation is performed onto an irradiation subject in a one-stroke writing manner. Also in the raster-scanning method, a beam spreads in a series-of-scanners manner. Therefore, in the case where a multi-leaf collimator is utilized in the raster-scanning method, the multi-leaf collimator 5 according to the foregoing embodiment demonstrates an effect. In other words, also in the case where an irradiation field is enlarged through a scanning method such as the spot-scanning method or the raster-scanning method, when the multi-leaf collimator 5 according to the embodiments of the present invention is utilized, there is demonstrated an effect that a penumbra is suppressed and a high-contrast irradiation field is formed.

Embodiment 5

There has been proposed a particle beam therapy system in which, for example, as disclosed in Patent Document 4, one of two scanning electromagnets is omitted, by contriving control method for a deflection electromagnet. However, even in the case of such an irradiation system, a deflection electromagnet for changing the orbit direction (the direction of the beam axis) replaces the omitted scanning electromagnet that scans a charged particle beam; therefore, the beam bundle has a series-of-scanners spread, whereby the multi-leaf collimator according to each of the foregoing embodiments demonstrates an effect of suppressing a penumbra.

Figure 8:
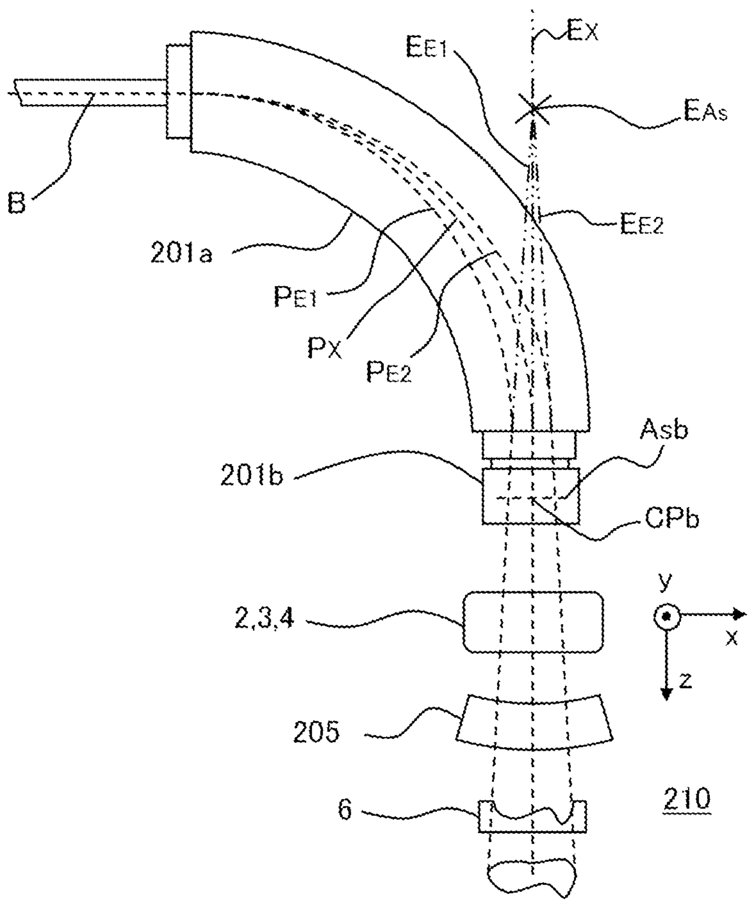
FIG. 8 is a view for explaining the configurations of a particle beam therapy system and a multi-leaf collimator according to Embodiment 5 of the present invention.

FIG. 8 is a view illustrating an irradiation system including a multi-leaf collimator in a particle beam therapy system according to Embodiment 5. In FIG. 8, the beam axis of a charged particle beam B supplied in the horizontal direction (the x direction) is deflected to the vertical direction by a deflection electromagnet 201*a* and passes through a scanning electromagnet 201*b*; then, as is the case in Embodiment 1, the charged particle beam B is irradiated onto an irradiation subject, by way of a ridge filter 2, a range shifter 3, a ring collimator 4, a multi-leaf collimator 205, and the bolus 6. The configuration of a particle beam therapy system 210 according to Embodiment 5 is the same as that of Embodiment 1, excluding the fact that instead of the scanning electromagnet 1*a* in the particle beam therapy system 10 according to Embodiment 1, the deflection electromagnet 201*a* is provided and that the setting reference for the shape and the orbit of the leaf plate of the multi-leaf collimator 205 is different.

In FIG. 8, inside the deflection electromagnet 201*a*, the charged particle beam B supplied in the horizontal direction is deflected in the z direction, while the beam axis $P_X$ draws an arc. In this situation, in the case of a normal deflection electromagnet, because control is performed in such a way that the magnetic field becomes constant, the beam bundle of the charged particle beam B does not spread; however, by periodically changing the magnetic field, the deflection electromagnet 201*a* scans the charged particle beam B in the x direction so that the beam bundle can spread in the x direction from $P_{E1}$ to $P_{E2}$. In other words, the deflection electromagnet 201*a* plays the role of the upstream scanning electromagnet 1*a* of Embodiment 1. The portion thereafter is basically the same as Embodiment 1; the scanning electromagnet 201*b* further spreads the beam bundle, which has been spread in the x direction, in the y direction.

This beam spreading manner can be regarded as a spreading manner at a time when the scanning axis of the upstream scanning electromagnet 201*a* exists at an equivalent reference point $E_{AS}$ in FIG. 8 and a beam, irradiated from the upper side along the beam axis $E_X$, is scanned in the x direction (including the z-direction component) and spreads in the x direction from $E_{E2}$ to $E_{E2}$. Because inside the deflection electromagnet 201*a*, the beam axis is gradually deflected as the beam advances, the beam axes (=beam axis $E_X$) at the entrance side and at the exit side are different from each other; thus, a scanning axis $E_{As}$ exists off the deflection electromagnet 201*a*. However, because the axis of a beam that enters the multi-leaf collimator 205 is the beam axis $E_X$, the reference point CPa that specifies the position of the scanning axis $E_{As}$ can be regarded as existing on the beam axis of the beam that enters the multi-leaf collimator 205, as a manner of thinking; therefore, the scanning axis $E_{As}$ can also be regarded as being perpendicular to the beam axis of the beam that enters the multi-leaf collimator 205. Accordingly, also in an irradiation system in which one of the electromagnets that perform scanning also plays the role of a deflection electromagnet, it may be allowed that the equivalent scanning axis $E_{As}$ is calculated based on the manner of beam spreading with respect to the beam axis of the beam that enters a multi-leaf collimator, and as is the case in Embodiment 1, the shape of the leaf plate of the multi-leaf collimator 205 and the orbit are set based on the equivalent scanning axis $E_{As}$ and the scanning axis $A_{sb}$ (the reference point CPb).

As can be seen from FIG. 8, in the case of an irradiation system in which one of the scanning electromagnets is omitted and instead of the omitted scanning electromagnet, the deflection electromagnet 201*a* that bends the orbit is utilized, the distance between the reference point CPb and the reference point (equivalent) CPa that specifies the equivalent scanning axis $E_{As}$ is wide in comparison with an ordinary irradiation system in which scanning is performed by an electromagnet dedicated to scanning (e.g., 1*a* and 1*b* in Embodiment 1). Accordingly, in the case of a multi-leaf collimator in which a beam is assumed to spread in a point-light-source manner, there is more conspicuously posed a problem that a penumbra is caused. However, the shape and the orbit of the leaf plate of the multi-leaf collimator 205 according to Embodiment 5 of the present invention are set in such a way that whatever penetration shape is formed, the direction of the plane on which the contour of the penetration shape is formed is the same as the direction of the beam spread. Therefore, the problem of a penumbra, which is conspicuously caused with an irradiation system in which one of the scanning electromagnets is omitted, can readily be solved.

As described above, in the particle beam therapy system 210 according to Embodiment 5, it is configured in such a way that scanning for one direction (x or y) out of the x-direction scanning and y-direction scanning is performed by the deflection electromagnet 201*a* that deflects the direction of a beam axis, and by regarding that the beam axis for setting the reference points CPa and CPb is the beam axis $E_X$ of the beam that enters the multi-leaf collimator 205, the configuration and the positioning of the multi-leaf collimator 205 are implemented; therefore, a penumbra can be suppressed and hence a high-contrast irradiation field can be formed.

Embodiment 6

In each of Embodiments 1 through 5, there have been explained the configurations of a multi-leaf collimator and an irradiation system utilizing the multi-leaf collimator and the beam orbit in the irradiation system. In Embodiment 6, there will be explained a treatment planning apparatus in which the operation conditions of a multi-leaf collimator and a particle beam therapy system according to each of the foregoing embodiments of the present invention are set.

Figure 9:
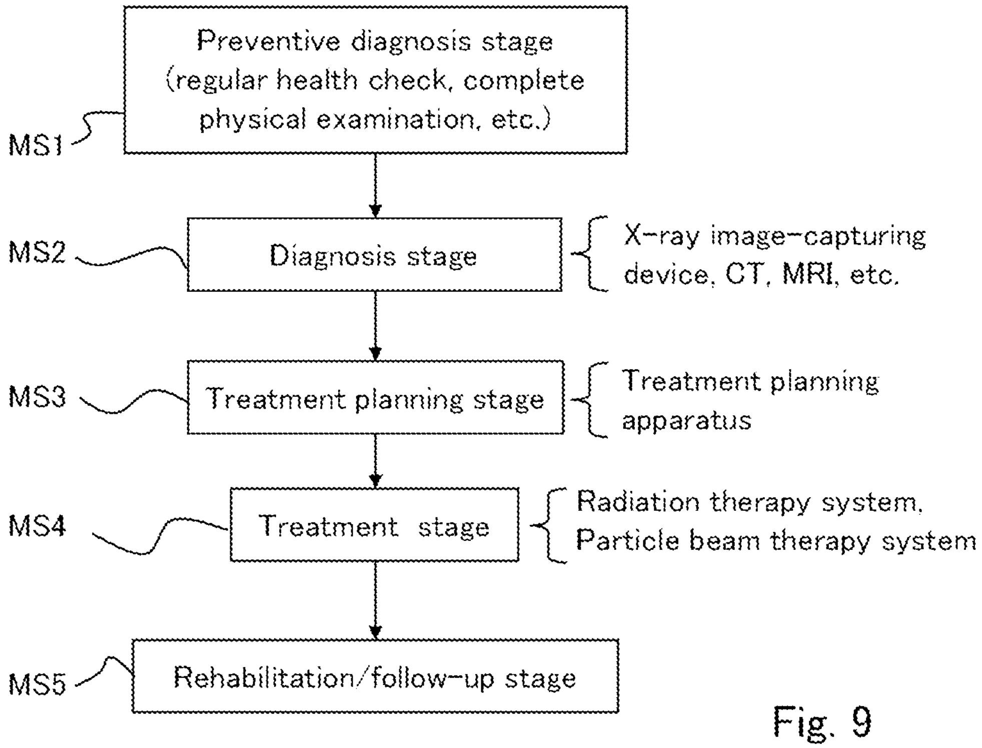
FIG. 9 is a diagram for explaining the flow of medical practice.

Here, before explaining a treatment planning apparatus, there will be explained medical practice on which a treatment plan to be implemented by the treatment planning apparatus is based. In general, it is conceivable that medical practice is configured with a number of stages. FIG. 9 represents the stages (flow) of medical practice by a flowchart and describes one or more apparatuses utilized in each stage. With reference to FIG. 9, the flow of a medical practice will be explained.

Specifically, medical practice may be roughly configured with a preventive diagnosis stage (MS1), a diagnosis stage (MS2), a treatment planning stage (MS3), a treatment stage (MS4), and a rehabilitation/follow-up stage (MS5). In particular, in a particle beam therapy or the like, the respective apparatuses utilized in the foregoing stages are those described in the right column of FIG. 9. For example, the apparatuses utilized in the diagnosis stage (MS2) are an X-ray image-capturing device, a CT (Computed Tomography), an MRI (Magnetic Resonance Imaging); the apparatus utilized in the treatment planning stage (MS3) is the one that is called a treatment planning apparatus. In addition, the apparatuses utilized in the treatment stage (MS4) are a radiation therapy system and a particle beam therapy system.

Next, each of the stages will be explained.

The preventive diagnosis stage (MS1) denotes a stage where a diagnosis is implemented preventively, regardless of whether or not there has been shown the onset of a disease. For example, a regular health check and a complete physical examination fall into this stage; with regard to a cancer, a method utilizing fluoroscopic imaging such as radiology, a method utilizing tomography such as PET (Positron Emission Tomography) or PET/CT, and a method utilizing a genetic test (immunological test) are known.

The diagnosis stage (MS2) denotes a stage where a diagnosis to be followed by a treatment is implemented after the onset of a disease. In the case of particle beam therapy, in order to implement a treatment, three-dimensional information on the position and the shape of a diseased site is required. Accordingly, there are utilized various kinds of CT and MRI that are capable of obtaining three-dimensional data on a diseased site.

The treatment planning stage (MS3) denotes a stage where a treatment plan is generated based on the result of the diagnosis. In the case of particle beam therapy, a treatment plan is generated, in this stage, by a treatment planning apparatus according to Embodiment 6. The treatment planning apparatus will be explained in detail later; here, the residual stage will be explained.

The treatment stage (MS4) denotes a stage where an actual treatment is performed based on the result of the treatment plan. In the case of particle beam therapy, a particle beam therapy system is utilized in this stage. A multi-leaf collimator according to each of the foregoing embodiments is utilized for forming an irradiation field in the irradiation system of a particle beam therapy system. In addition, in some cases, the treatment stage is completed with a single irradiation; however, usually, there are implemented a plurality of irradiations, each irradiation of which is performed every certain period.

The rehabilitation/follow-up stage (MS5) literally denotes a stage where rehabilitation is performed or there is performed a follow-up to check whether or not a disease has recurred. In the case of a cancer, in a follow-up of this stage, as is the case in the preventive diagnosis stage, a method utilizing fluoroscopic imaging such as radiology, a method utilizing tomography such as PET or PET/CT, or a method utilizing a genetic test (immunological test) is adopted.

As described above, in medical practice, the treatment planning is a series of works performed after the diagnosis stage and before the treatment stage. In a particle beam therapy system, a charged particle beam is irradiated based on a treatment plan obtained through a treatment planning apparatus; therefore, a treatment planning apparatus in particle beam therapy is provided with units that approximately play the following roles.

Role A: a unit for generating three-dimensional data, based on a plurality of image information items for an irradiation subject, which are preliminarily obtained.

Role B: a unit for generating an optimum irradiation condition (treatment planning draft) under given requirements.

Role C: a unit for simulating and displaying a final dose distribution for the optimum result (treatment planning draft).

In other words, a treatment planning apparatus is provided with a role in which in response to the result of a diagnosis, irradiation condition required for treatment is set; furthermore, the treatment planning apparatus has a unit that plays a role D of generating control data for the particle beam therapy system and the like, based on the set condition.

In order to play the foregoing roles, the treatment planning apparatus is specifically provided with the following functions.

<Role A>

Function a: a function for generating three-dimensional data based on a tomographic image obtained in the diagnosis stage.

Function b: a function for displaying the generated three-dimensional data as seen from various viewing points, as is the case with a three-dimensional CAD.

Function c: a function for distinguishing a diseased site from normal tissues and storing them in the generated three-dimensional data.

<Role B>

Function d: a function for setting parameters for a particle beam therapy system utilized in the treatment stage and for simulating irradiation.

Function e: a function for optimizing irradiation under the requirements set by a user of the apparatus.

<Role C>

Function f: a function for displaying the optimized irradiation result in such a way as to be superimposed on the three-dimensional data.

<Role D>

Function g: a function for setting the shapes, of a multi-leaf collimator and a bolus, for realizing the optimized irradiation (this function is a one when broad-beam irradiation is anticipated, and includes a case of multi-port irradiation).

Function h: a function for setting the beam irradiation orbit for realizing the optimized irradiation (when scanning irradiation is anticipated).

Function i: a function for generating a driving code, for a particle beam therapy system, for realizing the beam irradiation orbit.

<Others>

Function j: a function for storing various kinds of data items generated in the apparatus.

Function k: a function capable of reading various kinds of data items stored in the past and reusing past information.

There will be explained the system configuration of a treatment planning apparatus for realizing the foregoing functions. In recent years, almost no manufacturer of a treatment planning apparatus has designed and manufactured dedicated hardware; the hardware is configured based on a commercially available Unix (registered trademark) workstation or a PC, and as peripheral devices, universal devices are utilized in many cases. That is to say, manufacturers of treatment planning apparatuses primarily develop, manufacture, and sell treatment planning software. In the treatment planning software, for example, there is prepared a module for realizing the functions a through k, as a subprogram to be called by main program. By omitting, as may be necessary, the flow between the function a and the function k or re-implementing it by changing the requirements, the user of a treatment planning apparatus can generate a treatment plan while calling necessary modules.

Next, while advancing the explanation to the functions or the modules for realizing those functions, there will be explained a treatment planning apparatus according to Embodiment 6.

Function a (module a) generates three-dimensional data based on a series of tomographic images obtained in the diagnosis stage. It is desirable that when a tomographic image is read, patient information such as a patient ID and scanning information (such as a slice interval, a slice thickness, FOV, and a tomographic condition) are also read in a corresponding manner. Here, the three-dimensional data denotes information required for virtually and three-dimensionally reproducing an imaging subject including a diseased site in a treatment planning apparatus. In general, there is utilized a method in which a virtual space is defined in a treatment planning apparatus, points are arranged within the virtual space in such a way as to be spaced evenly apart from one another and in a lattice-like manner, and the respective material information items, which are obtained from a tomographic image, are positioned at the corresponding points. The reason why Function a is required is that one of the biggest objects of a treatment planning apparatus is to simulate treatment, and for that purpose, it is necessary to reproduce a diseased site, which is an irradiation subject, and the peripheral tissues thereof.

Function b (module b) displays the generated three-dimensional data as seen from various viewing points, as is the case with a three-dimensional CAD.

Function c (module c) distinguishes a diseased site from normal tissues and stores them in the generated three-dimensional data. For example, it is assumed that a tomographic image is obtained through X-ray CT. In this case, the "material information" utilized in Function a corresponds to the radiolucency of an X-ray. That is to say, the three-dimensional model reproduced in the virtual space from this tomographic image represents the shape of a three-dimensional body formed of materials whose radiolucencies are different from one another. In the virtual space of a treatment planning apparatus, the "material information", i.e., the X-ray radiolucency is rendered by changing the color and the brightness. Furthermore, this "material information" makes it possible to understand that this part of the three-dimensional model reproduced in the virtual space corresponds to a bone or that part corresponds to a tumor, and a diseased site is distinguished from normal tissues. The result of the distinction between a diseased site and normal tissues can be stored in a storage device (such as a hard disk) of the treatment planning apparatus.

Function d (module d) sets parameters for a particle beam therapy system utilized in the treatment stage and simulates irradiation. The parameters for a particle beam therapy system denote geometric information on the particle beam therapy system and information on an irradiation field. The geometric information includes the position of the isocenter, the position of the bed, and the like. The information on an irradiation field includes the foregoing "coordinates of the reference point CPa and the coordinates of the reference point CPb" and the like. The parameters include the width (thickness) of the leaf plate $\mathbf{5}_L$ of the multi-leaf collimator 5 or 205 (hereinafter, only "5", representing both, is expressed), the number of the leaf plates $\mathbf{5}_L$, the traveling distance (angle) of the leaf plate $\mathbf{5}_L$, and the like.

Function e (module e) optimizes irradiation under the requirements set by a user of the treatment planning apparatus.

Function f (module f) displays the optimized irradiation result in such a way as to be superimposed on the three-dimensional data.

Function g (module g) sets the shapes, of the multi-leaf collimator 5 and the bolus 6, for realizing the optimized irradiation. This function is a one when broad-beam irradiation is anticipated, and includes a case of multi-port irradiation.

Function h (module h) sets the beam irradiation orbit for realizing the optimized irradiation. This function is a one when scanning such as spot scanning or raster scanning is anticipated.

Function I (module i) generates a driving code, for a particle beam therapy system, for realizing the beam irradiation orbit. In this situation, when as described later, a coordinate system conforming to a series-of-scanners spread is adopted, there can readily be generated a driving code for realizing an opening shape (penetration shape SP) corresponding to the obtained optimum irradiation plan for the multi-leaf collimator 5 according to each of Embodiments 1 through 5.

Function j (module j) stores various kinds of data items set and generated in the apparatus.

Function k (module k) can read various kinds of data items stored in the past and reuse past information.

<Coordinate System Conforming Series-of-Scanning Spread>

In a conventional treatment planning apparatus, the three-dimensional data utilized in Function a and functions following to Function a are represented by an orthogonal coordinate system (xyz coordinate system). In the case of a multi-leaf collimator whose total shape is a conventional rectangular parallelepiped, the leaf driving direction thereof is also represented by an orthogonal-coordinate direction (for example, the x direction and the y direction); therefore, it is convenient to represent the three-dimensional data by an orthogonal coordinate system. That is because leaf driving data and shape data for generating the shape of the opening portion in such a way as to coincide with the shape of a diseased site coincide with each other.

On the other hand, in the case of the multi-leaf collimator 5 according to the present invention, it is desirable that because the drive of the leaf plate 5L is performed in a curvilinear manner, the command value for driving the leaf is given as an angle with respect to the reference point. That is to say, it is desired that the shape data for forming the shape of the opening portion in accordance with the shape of a diseased site includes an angle, with respect to the reference point, that is in the same format as the leaf driving command value of the present invention.

Thus, the treatment planning apparatus according to Embodiment 6 of the present invention is configured in such a way that the three-dimensional data for a diseased site is represented by a special coordinate system.

Specifically, it is a special coordinate system represented by the following definition (D1).

$$[\psi_a, \psi_b, r_b] \tag{D1}$$

where $\psi_a$ is a beam deflection angle with respect to the reference axis ($A_{sa}$) that is perpendicular to the beam axis $X_B$ and passes through the reference point CPa, $\psi_b$ is a beam deflection angle with respect to the reference axis ($A_{sb}$) that is perpendicular to the beam axis $X_B$ and the reference axis $A_{sa}$ and passes through the reference point CPb, and $r_b$ is a distance between the reference point CPb (or the reference axis $A_{sb}$) and the irradiation point.

An arbitrary point in the three-dimensional space can uniquely be represented by the foregoing three information items. In this regard, however, it is required to preliminarily determine the reference points CPa and CPb in accordance with the arrangement of the scanning electromagnets 1$a$ and 1$b$. Instead of $r_b$, there may be utilized a beam propagation distance $r_a$ between the reference point CPa (or the reference axis (Asa)) and the irradiation point.

Here, it is assumed that the isocenter, which is an irradiation reference, is utilized as the origin of the xyz coordinate system, and the xyz coordinates of the reference point CPa and the xyz coordinates of the reference point CPb are given as follows.

reference point CPa: $(0, 0, -1_a)$ reference point CPb: $(0, 0, -1_b)$

Then, it is assumed that as illustrated in FIGS. 1 through 3, the upstream scanning electromagnets 1$a$ and the downstream scanning electromagnet 1$b$ are the x-direction scanning electromagnet and the y-direction scanning electromagnet, respectively. In this situation, when the coordinates of a certain point is given by $[\psi_a, \psi_b, r_b]$ represented by use of the special coordinate system described in the definition (D1), the x coordinate, the y coordinate, and the z coordinate of this point are given by the following equation (4).

$$\begin{bmatrix} x \\ y \\ z \end{bmatrix} = Rot_x(\varphi_b)\left\{Rot_y(\varphi_a)\begin{bmatrix} 0 \\ 0 \\ l_a - l_b + r_b \end{bmatrix} - \begin{bmatrix} 0 \\ 0 \\ l_a - l_b \end{bmatrix}\right\} - \begin{bmatrix} 0 \\ 0 \\ l_b \end{bmatrix} \tag{4}$$

Here, when $Rot_x(\psi_b)$, and $Rot_y(\psi_a)$ in the equation (4) are defined as in (D2), the xyz coordinates of this certain point is obtained as in the equation (5).

$$Rot_x(\varphi_b) = \begin{bmatrix} 1 & 0 & 0 \\ 0 & \cos\varphi_b & -\sin\varphi_b \\ 0 & \sin\varphi_b & \cos\varphi_b \end{bmatrix}, \quad Rot_y(\varphi_a) = \begin{bmatrix} \cos\varphi_a & 0 & \sin\varphi_a \\ 0 & 1 & 0 \\ -\sin\varphi_a & 0 & \cos\varphi_a \end{bmatrix} \tag{D2}$$

$$\begin{aligned} \begin{bmatrix} x \\ y \\ z \end{bmatrix} &= Rot_x(\varphi_b)\left\{\begin{bmatrix} (l_a - l_b + r_b)\sin(\varphi_a) \\ 0 \\ (l_a - l_b + r_b)\cos(\varphi_a) \end{bmatrix} - \begin{bmatrix} 0 \\ 0 \\ l_a - l_b \end{bmatrix}\right\} - \begin{bmatrix} 0 \\ 0 \\ l_b \end{bmatrix} \\ &= \begin{bmatrix} (l_a - l_b + r_b)\sin(\varphi_a) \\ -\sin(\varphi_b)\{(l_a - l_b + r_b)\cos(\varphi_a) - (l_a - l_b)\} \\ \cos(\varphi_b)\{(l_a - l_b + r_b)\cos(\varphi_a) - (l_a - l_b)\} \end{bmatrix} - \begin{bmatrix} 0 \\ 0 \\ l_b \end{bmatrix} \\ &= \begin{bmatrix} (l_a - l_b + r_b)\sin(\varphi_a) \\ -\sin(\varphi_b)\{(l_a - l_b + r_b)\cos(\varphi_a) - (l_a - l_b)\} \\ \cos(\varphi_b)\{(l_a - l_b + r_b)\cos(\varphi_a) - (l_a - l_b)\} - l_b \end{bmatrix} \end{aligned} \tag{5}$$

On the contrary, the method of obtaining the special coordinate system from the xyz coordinate system is described below.

Because $1_b$ is a given value that is inherent to an irradiation system, $\psi_b$ can be obtained, as in the equation (6), from the relationship between y and z in the equation (5).

$$\frac{-y}{z + l_b} = \frac{\sin\varphi_b}{\cos\varphi_b} = \tan\varphi_b \qquad \therefore \varphi_b = \arctan\left(\frac{-y}{z + l_b}\right) \tag{6}$$

Because being also a given value that is inherent to an irradiation system, $1_a$ can be defined, as in the definition (D3), from the relationship between y and z in the equation (5); thus, from the relationship with z in the equation (5) and the definition (D3), $\psi_a$ can be obtained from the equation (7).

$$\Lambda := y^2 + (z + l_b)^2 + (l_a - l_b) = (l_a - l_b + r_b)\cos\psi_a \quad \text{(D3)}$$

$$\frac{x}{\Lambda} = \frac{\sin\varphi_a}{\cos\varphi_a} = \tan\varphi_a \quad (7)$$

$$\therefore \varphi_a = \arctan\left(\frac{x}{\Lambda}\right)$$

Lastly, $r_b$ can be obtained from the equation (8).

$$x^2+\Lambda^2=l_a-l_b+r_b)^2$$

$$\therefore r_b=\sqrt{x^2+\Lambda^2}-(l_a-l_b) \quad (8)$$

There is provided a coordinate transformation function in which the coordinate system [$\psi_a$, $\psi_b$, $r_b$] conforming to the foregoing series-of-scanners spread is utilized already from the stage of Function a, i.e., as Function a or as an auxiliary function for implementing Function a, there is performed transformation to a special coordinate system, under the assumption of series-of-scanners.

Figure 10:
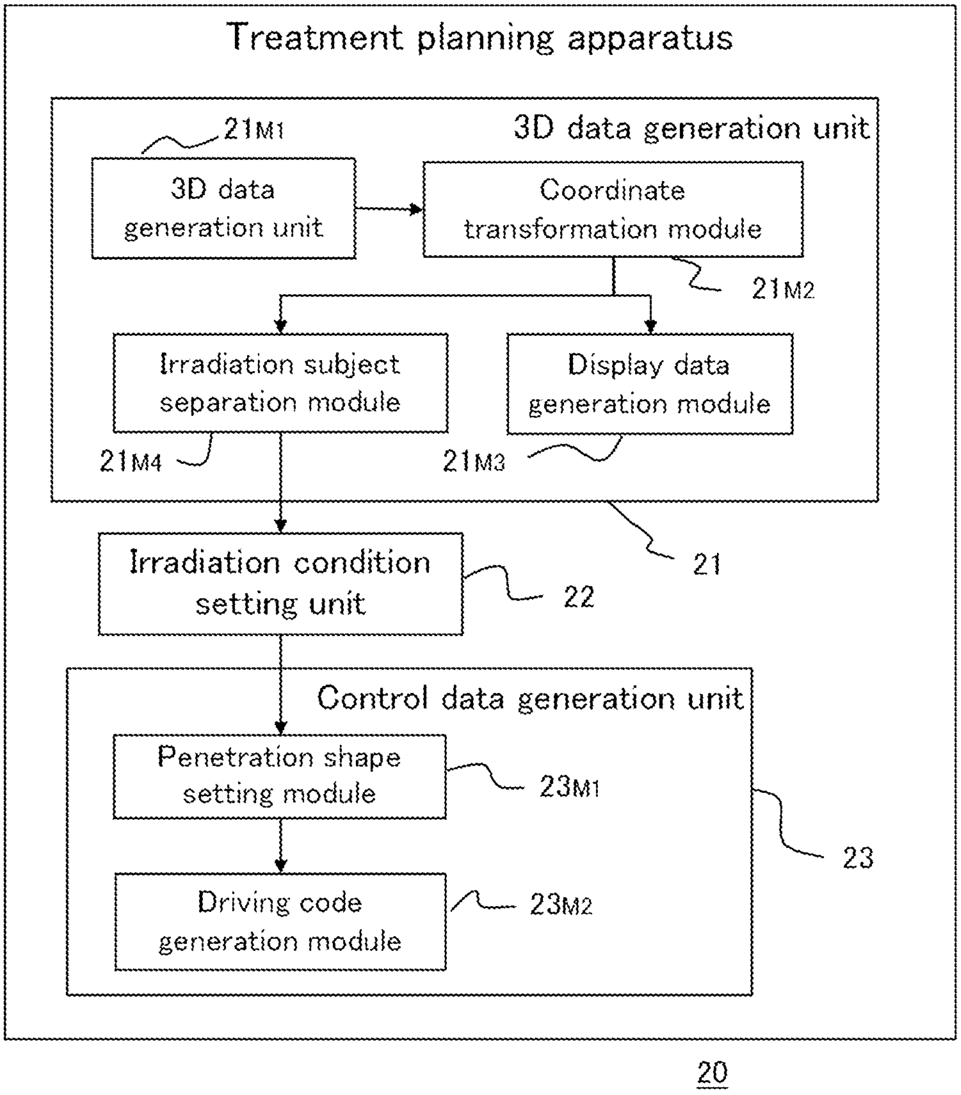
FIG. 10 is a block diagram for explaining the configuration of a treatment planning apparatus according to Embodiment 6 of the present invention.

For example, FIG. 10 illustrates, with a block diagram, the characteristic parts in the roles (units) and the functions (modules) of a treatment planning apparatus according to Embodiment 6 of the present invention. In FIG. 10, a treatment planning apparatus 20 is provided with a three-dimensional data generation unit 21 for generating three-dimensional data from image data on a diseased site, which is an irradiation subject; the irradiation condition setting unit 22 for setting an irradiation condition, based on the generated three-dimensional data; and a control data generation unit 23 for generating control data for a particle beam therapy system, based on the set irradiation condition. As described above, these units and modules are formed in a computer by software; thus, these parts are not physically formed.

The three-dimensional data generation unit 21 is provided with a three-dimensional data generation module $\mathbf{21}_{M1}$ for, as Function a, generating three-dimensional data on a diseased site, a body shape, and the like; a coordinate transformation module $\mathbf{21}_{M2}$ for transforming the generated three-dimensional data into data in the coordinate system [$\psi_a$, $\psi_b$, $r_b$] represented through the definition (D1) under the assumption of series-of-scanners; a display data generation module $\mathbf{21}_{M3}$ for, as Function b, generating display data, based on the transformed data; and an irradiation subject separation module $\mathbf{21}_{M4}$ for distinguishing a diseased site, which is an irradiation subject, from normal tissues, based on the transformed data. As Role A, the three-dimensional data generation unit 21 generates, from image information, three-dimensional data in the coordinate system represented through the definition (D1).

As Function B, the irradiation condition setting unit 22 sets, through the functions d and e, an optimum irradiation condition, based on three-dimensional data in the coordinate system represented through the definition (D1). The control data generation unit 23 is provided with a penetration shape setting module $\mathbf{23}_{M1}$ that sets, as the function g, the penetration shape PS to be formed by the multi-leaf collimator 5 based on at least the set irradiation condition; and a driving code generation module $\mathbf{23}_{M2}$ that generates, as the function i, a respective driving code for the leaf plates 5L of the multi-leaf collimator 5 based on the set penetration shape. As Role D, the control data generation unit 23 generates at least control data for the multi-leaf collimator 5 in the coordinate system represented through the definition (D1), based on the set irradiation condition.

Accordingly, in the three-dimensional data generation unit 21 and the irradiation condition setting unit 22, three-dimensional data, in the coordinate system represented through the definition (D1), for determining the irradiation position is specified by use of a beam deflection angle with respect to the reference axis ($A_{sa}$) that is perpendicular to at least the beam axis $X_B$ and passes through the reference point CPa, and a beam deflection angle with respect to the reference axis ($A_{sb}$) that is perpendicular to the beam axis $X_B$ and the reference axis $A_{sa}$ and passes through the reference point CPb. Thus, the driving code for the multi-leaf collimator 5 generated by the control data generation unit 23 becomes such a driving code as realizes the opening shape (penetration shape PS) conforming to the optimum irradiation plan obtained in the irradiation condition setting unit 22. In other words, in the treatment planning apparatus 20 according to Embodiment 6 of the present invention, a function for conversion into a special coordinate system in which series-of-scanners is anticipated is provided in the functions (modules) for playing the roles of a treatment plan, and three-dimensional data is specified in the special coordinate system. As a result, the shape data for generating the shape of the opening portion in accordance with the shape of a diseased site and the leaf driving command value can be represented by a same format including angles with respect to the reference point (one of the angles is for selecting the leaf plate 5L, among the leaf rows 5*c*, that has a facing side PL whose angle is near to the angle). Accordingly, in an irradiation system in which a beam spreads in a series-of-scanners manner, a driving code for optimally controlling the multi-leaf collimator 5 can readily be generated.

Therefore, in the treatment planning apparatus 20 according to Embodiment 6 of the present invention, for a particle beam therapy system utilizing the foregoing multi-leaf collimator 5 (or 205) capable of suppressing a penumbra for an irradiation system in which a particle beam spreads in a series-of-scanners manner, the leaf driving command value for forming the shape of the opening portion in accordance with the shape of a diseased site can be generated by directly utilizing the three-dimensional data inputted to and outputted from the treatment planning apparatus 20.

As described above, the treatment planning apparatus 20 according to Embodiment 6 is configured in such a way as to include the three-dimensional data generation unit 21 for generating three-dimensional data from image data on a diseased site, which is an irradiation subject; the irradiation condition setting unit 22 for setting an irradiation condition, based on the generated three-dimensional data; and the control data generation unit 23 for generating at least the control data, among control data items for a particle beam therapy system, that is for the multi-leaf collimator 5 according to one of Embodiments 1 through 5, based on a set irradiation condition. In addition, the treatment planning apparatus 20 according to Embodiment 6 is configured in such a way that the three-dimensional data generation unit 21 generates the three-dimensional data through a coordinate system that is specified by the beam deflection angle $\psi_a$ with respect to the reference axis $A_{sa}$ that is perpendicular to the beam axis $X_B$ and passes through the reference point CPa, the beam deflection angle $\psi_b$ with respect to the reference axis $A_{sb}$ that is perpendicular to the beam axis $X_B$ and the reference axis $A_{sa}$ and passes through the reference point CPb, and the distance r from the reference axis $A_{sa}$ or $A_{sb}$, or from the reference point CPa or CPb. As a result, the leaf driving command value for forming the shape of the opening portion in accordance with the shape of a diseased site can be generated by directly utilizing the three-dimensional data that is inputted to or outputted from the treatment planning apparatus 20. In other words, in the control data generation unit 23, the control data can be specified by two deflection angles $\psi_a$ and $\psi_b$; therefore, in a particle beam therapy system that can suppress a penumbra in an irradiation system in which a particle beam spreads in a series-of-scanners manner and that can irradiate a high-contrast and an excellent beam, it is made possible to perform a high-contrast and high-accuracy irradiation.

DESCRIPTION OF REFERENCE NUMERALS

1: wobbler electromagnet
1*a*: x-direction (upstream) scanning electromagnet
1*b*: y-direction (downstream) scanning electromagnet
2: ridge filter
3: range shifter
4: ring collimator
5: multi-leaf collimator
$5_L$: leaf plate
$5_G$: leaf group
$5_D$: leaf driving unit
6: bolus
10: particle beam therapy system
20: treatment planning apparatus
21: three-dimensional data generation unit
22: irradiation condition setting unit
23: control data generation unit
$A_{sa}$: scanning axis (1st axis) of upstream scanning electromagnet ($E_{As}$: virtual axis)
$A_{sb}$: scanning axis (2nd axis) of downstream scanning electromagnet
CPa: 1st reference point
CPb: 2nd reference point
$E_L$: facing end face of leaf plate
$F_B$: beam bundle (spread) of particle beam
OL: driving orbit of leaf plate
$P_I$: beam-incident-side end face (adjacent to $E_L$) of leaf plate
$P_L$: thickness-direction facing side of leaf plate
PS: penetration shape
$P_x$: beam-emission-side end face (adjacent to $E_L$) of leaf plate
ST: scanning locus of particle beam
$X_B$: beam axis of particle beam
($E_x$: beam axis of beam entering multi-leaf collimator)
Three-digit numbers each denote variant examples in Embodiments.

The invention claimed is:

1. A multileaf collimator that is disposed on a beam orbit of an accelerated charged particle beam and that limits or forms an irradiation field of the charged particle beam in such a way that the irradiation field conforms to an irradiation subject, the multileaf collimator comprising:

a leaf row in which a plurality of leaf plates are arranged in the thickness direction thereof in such a way that the respective one end faces of the leaf plates are trued up; and a leaf plate drive mechanism that drives each of the plurality of leaf plates in such a way that the one end face approaches or departs from a beam axis of the charged particle beam, wherein each of the plurality of leaf plates has at least one curved surface having two different curvature radiuses in respective directions, wherein a first axis that is the center axis of one curvature radius out of the two curvature radiuses passes through a first reference point on the beam axis, and wherein a second axis that is the center axis of the other curvature radius passes through a second reference point that is on the beam axis and apart from the first reference point.

2. The multileaf collimator according to claim 1, wherein one of the curved surfaces having two different curvature radiuses in the respective directions is an endface corresponding to the bottom surface portion of the multileaf collimator.

3. The multileaf collimator according to claim 1, wherein one of the curved surfaces having two different curvature radiuses in the respective directions is an endface corresponding to the top surface portion of the multileaf collimator.

4. The multileaf collimator according to claim 2, wherein one of the curved surfaces having two different curvature radiuses in the respective directions is an endface corresponding to the top surface portion of the multileaf collimator.

5. A particle beam therapy system comprising:

an irradiation nozzle that scans a particle beam supplied from an accelerator, by use of two electromagnets whose scanning directions are different from each other, and that irradiates the particle beam in such a way as to enlarge an irradiation field; and a multi-leaf collimator according to claim 1, disposed in a particle beam irradiated from the irradiation nozzle, wherein the multi-leaf collimator is disposed in such a way that the first axis coincides with the scanning axis of one of the two electromagnets and the second axis coincides with the scanning axis of the other one of the two electromagnets.

6. A particle beam therapy system comprising:

an irradiation nozzle that scans a particle beam supplied from an accelerator, by use of two electromagnets whose scanning directions are different from each other, and that irradiates the particle beam in such a way as to enlarge an irradiation field; and a multi-leaf collimator according to claim 2, disposed in a particle beam irradiated from the irradiation nozzle, wherein the multi-leaf collimator is disposed in such a way that the first axis coincides with the scanning axis of one of the two electromagnets and the second axis coincides with the scanning axis of the other one of the two electromagnets.

7. A particle beam therapy system comprising:

an irradiation nozzle that scans a particle beam supplied from an accelerator, by use of two electromagnets whose scanning directions are different from each other, and that irradiates the particle beam in such a way as to enlarge an irradiation field; and a multi-leaf collimator according to claim 3, disposed in a particle beam irradiated from the irradiation nozzle, wherein the multi-leaf collimator is disposed in such a way that the first axis coincides with the scanning axis of one of the two electromagnets and the second axis coincides with the scanning axis of the other one of the two electromagnets.

8. A particle beam therapy system comprising:

an irradiation nozzle that scans a particle beam supplied from an accelerator, by use of two electromagnets whose scanning directions are different from each other, and that irradiates the particle beam in such a way as to enlarge an irradiation field; and a multi-leaf collimator according to claim 4, disposed in a particle beam irradiated from the irradiation nozzle, wherein the multi-leaf collimator is disposed in such a way that the first axis coincides with the scanning axis of one of the two electromagnets and the second axis coincides with the scanning axis of the other one of the two electromagnets.

9. The particle beam therapy system according to claim 5, wherein the irradiation nozzle enlarges the irradiation field through a spiral Wobbling method.

10. The particle beam therapy system according to claim 5, wherein the irradiation nozzle enlarges the irradiation field through a scanning method.

11. The particle beam therapy system according to claim 5, wherein scanning for one direction out of the two directions is performed by a deflection electromagnet that deflects the direction of a beam axis, and the beam axis on which the first position and the second position are set is the beam axis of a beam that enters the multi-leaf collimator.

12. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 5, based on the set irradiation condition, wherein the three-dimensional data generation unit generates the three-dimensional data by utilizing at least a beam deflection angle with respect to the first axis and a beam deflection angle with respect to the second axis.

13. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 6, based on the set irradiation condition, wherein the three-dimensional data generation unit generates the three-dimensional data by utilizing at least a beam deflection angle with respect to the first axis and a beam deflection angle with respect to the second axis.

14. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 7, based on the set irradiation condition, wherein the three-dimensional data generation unit generates the three-dimensional data by utilizing at least a beam deflection angle with respect to the first axis and a beam deflection angle with respect to the second axis.

15. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 8, based on the set irradiation condition, wherein the three-dimensional data generation unit generates the three-dimensional data by utilizing at least a beam deflection angle with respect to the first axis and a beam deflection angle with respect to the second axis.

16. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 9, based on the set irradiation condition, wherein the three-dimensional data generation unit generates the three-dimensional data by utilizing at least a beam deflection angle with respect to the first axis and a beam deflection angle with respect to the second axis.

17. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 10, based on the set irradiation condition, wherein the three-dimensional data generation unit generates the three-dimensional data by utilizing at least a beam deflection angle with respect to the first axis and a beam deflection angle with respect to the second axis.

18. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 11, based on the set irradiation condition, wherein the three-dimensional data generation unit generates the three-dimensional data by utilizing at least a beam deflection angle with respect to the first axis and a beam deflection angle with respect to the second axis.

19. A multileaf collimator that is disposed on a beam orbit of an accelerated charged particle beam and that limits or forms an irradiation field of the charged particle beam in such a way that the irradiation field conforms to an irradiation subject, the multileaf collimator comprising:

a leaf row in which a plurality of leaf plates are arranged in the thickness direction thereof in such a way that the respective one end faces of the leaf plates are trued up; and a leaf plate drive mechanism that drives each of the plurality of leaf plates in such a way that the one end face approaches or departs from a beam axis of the charged particle beam, wherein each of the plurality of leaf plates is formed of part of a ring that is created (1) by rotating a cross section surrounded by two arcs that are (i) coaxial with each other with respect to a first axis including a first reference point, and (ii) have respective different radiuses, and (2) by rotating two straight lines that are on a plane perpendicular to the first axis and extend from the first reference point around a second axis that is (i) on the beam axis, (ii) includes a second reference point being apart from the first reference point, and (iii) has a direction different from that of the first axis.

20. A particle beam therapy system comprising:

an irradiation nozzle that scans a particle beam supplied from an accelerator, by use of two electromagnets whose scanning directions are different from each other, and that irradiates the particle beam in such a way as to enlarge an irradiation field; and a multi-leaf collimator according to claim 19, disposed in a particle beam irradiated from the irradiation nozzle, wherein the multi-leaf collimator is disposed in such a way that the first axis coincides with the scanning axis of one of the two electromagnets and the second axis coincides with the scanning axis of the other one of the two electromagnets.

21. A treatment planning apparatus comprising:

a three-dimensional data generation unit for generating three-dimensional data from image data on an irradiation subject;

an irradiation condition setting unit that sets an irradiation condition, based on the generated three-dimensional data; and a control data generation unit that generates control data for controlling leaf driving for the multi-leaf collimator in the particle beam therapy system according to claim 20, based on the set irradiation condition, wherein the three-dimensional data generation unit generates the three-dimensional data by utilizing at least a beam deflection angle with respect to the first axis and a beam deflection angle with respect to the second axis.

* * * * *